US012653997B2

(12) United States Patent
Prasad et al.

(10) Patent No.: US 12,653,997 B2
(45) Date of Patent: Jun. 16, 2026

(54) UNIVERSAL CAPS INCLUDING INTERFERING PROTRUSIONS FOR INTERFERENCE ENGAGEMENT TO MEDICAL CONNECTORS

(71) Applicant: Becton, Dickinson and Company, Franklin Lakes, NJ (US)

(72) Inventors: Shishir Prasad, Ramsey, NJ (US); Balaji K, Chennai (IN); Prasad Govindaraj, Coimbatore (IN); Sridhaar Nandakumar, Chennai (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 708 days.

(21) Appl. No.: 17/981,013

(22) Filed: Nov. 4, 2022

(65) Prior Publication Data

US 2024/0149039 A1     May 9, 2024

(51) Int. Cl.
*A61M 39/16* (2006.01)
*A61M 39/20* (2006.01)

(52) U.S. Cl.
CPC .......... *A61M 39/162* (2013.01); *A61M 39/20* (2013.01); *A61M 2207/10* (2013.01)

(58) Field of Classification Search
CPC .... A61M 39/20; A61M 39/162; A61M 39/16; A61M 39/165; A61M 2207/10
See application file for complete search history.

(56) References Cited

U.S. PATENT DOCUMENTS

| | | |
|---|---|---|
| 7,806,890 B2 | 10/2010 | McKinnon et al. |
| 8,671,496 B2 | 3/2014 | Vaillancourt et al. |
| 8,696,820 B2 | 4/2014 | Vaillancourt et al. |
| 8,740,864 B2 | 6/2014 | Hoang et al. |
| 9,039,989 B2 | 5/2015 | Liu et al. |
| 9,283,369 B2 | 3/2016 | Ma et al. |
| 9,399,125 B2 | 7/2016 | Burkholz |
| 9,480,833 B2 | 11/2016 | Hoang et al. |
| D834,187 S | 11/2018 | Ryan |
| 10,376,686 B2 | 8/2019 | Burkholz et al. |
| 10,413,716 B2 | 9/2019 | Sathe |
| 10,871,246 B2 | 12/2020 | Marici et al. |

(Continued)

FOREIGN PATENT DOCUMENTS

| | | |
|---|---|---|
| EP | 3142711 B1 | 1/2019 |
| WO | 2021026199 A1 | 2/2021 |

*Primary Examiner* — Courtney D Heinle
*Assistant Examiner* — Andrew Thanh Bui
(74) *Attorney, Agent, or Firm* — Servilla Whitney LLC

(57) ABSTRACT

A cap configured to engage at least a first connector and a second connector of different types includes a housing having a first end, an open second end, a sidewall extending between the first end and the second end, and a plurality of interfering protrusions extending inwardly from an inner surface of the sidewall configured to provide an interference engagement with the first connector or the second connector. The cap also includes an absorbent support positioned in the housing configured to contact portions of the first connector or the second connector, when the first connector or the second connecter is inserted into the housing and a seal mounted to a portion of the absorbent support configured to cover an opening of the first connector or the second connector when the first connector or the second connector is inserted into the housing.

21 Claims, 13 Drawing Sheets

(56)  References Cited

U.S. PATENT DOCUMENTS

| | | | |
|---|---|---|---|
| 11,083,883 B2 | 8/2021 | Ryan et al. | |
| 11,273,298 B2 | 3/2022 | Erekovcanski et al. | |
| 11,344,715 B2 | 5/2022 | Erekovcanski et al. | |
| 11,389,636 B2 | 7/2022 | Coyle | |
| 11,628,288 B1 * | 4/2023 | Solomon | A61M 39/18 |
| | | | 604/533 |
| 11,779,520 B1 * | 10/2023 | Vitello | A61J 1/18 |
| | | | 604/256 |
| 2010/0049170 A1 * | 2/2010 | Solomon | A61M 39/165 |
| | | | 604/539 |
| 2012/0302968 A1 | 11/2012 | Tennican | |
| 2012/0302997 A1 | 11/2012 | Gardner et al. | |
| 2013/0035667 A1 | 2/2013 | Anderson et al. | |
| 2013/0178804 A1 | 7/2013 | Tennican | |
| 2013/0197485 A1 | 8/2013 | Gardner et al. | |
| 2014/0135739 A1 | 5/2014 | Solomon et al. | |
| 2015/0005699 A1 | 1/2015 | Burbank et al. | |
| 2015/0086441 A1 | 3/2015 | She et al. | |
| 2016/0106968 A1 | 4/2016 | Solomon et al. | |
| 2016/0144118 A1 | 5/2016 | Solomon et al. | |
| 2016/0310720 A1 | 10/2016 | Solomon et al. | |
| 2017/0203092 A1 * | 7/2017 | Ryan | A61B 90/70 |
| 2018/0055962 A1 | 3/2018 | Drmanovic | |
| 2018/0064604 A1 | 3/2018 | Drmanovic | |
| 2018/0071508 A1 | 3/2018 | Drmanovic | |
| 2018/0085568 A1 | 3/2018 | Drmanovic | |
| 2018/0200500 A1 | 7/2018 | Ziebol et al. | |
| 2018/0214242 A1 | 8/2018 | Davis et al. | |
| 2018/0214684 A1 | 8/2018 | Avula et al. | |
| 2018/0250194 A1 | 9/2018 | Drmanovic | |
| 2018/0256804 A1 | 9/2018 | Burbank et al. | |
| 2018/0256880 A1 | 9/2018 | Follman et al. | |
| 2018/0256881 A1 | 9/2018 | Hitchcock et al. | |
| 2018/0256883 A1 | 9/2018 | Follman et al. | |
| 2018/0369562 A1 | 12/2018 | Gardner et al. | |
| 2019/0038888 A1 | 2/2019 | Gardner | |
| 2019/0099593 A1 | 4/2019 | Avula et al. | |
| 2019/0117332 A1 | 4/2019 | Davis et al. | |
| 2019/0201681 A1 | 7/2019 | Ziebol et al. | |
| 2019/0262525 A1 | 8/2019 | Wyeth et al. | |
| 2019/0282795 A1 | 9/2019 | Fangrow | |
| 2019/0351212 A1 | 11/2019 | Dudar et al. | |
| 2020/0121858 A1 | 4/2020 | Anderson et al. | |
| 2020/0139037 A1 | 5/2020 | Ziebol et al. | |
| 2020/0155794 A1 | 5/2020 | Ziebol | |
| 2020/0197686 A1 | 6/2020 | Anderson et al. | |
| 2020/0238070 A1 | 7/2020 | Ryan | |
| 2021/0001110 A1 | 1/2021 | Bedoe et al. | |
| 2021/0048128 A1 | 2/2021 | Marici et al. | |
| 2021/0093791 A1 | 4/2021 | Anderson et al. | |
| 2021/0138225 A1 | 5/2021 | Jiang et al. | |
| 2021/0275707 A1 | 9/2021 | Jiang et al. | |
| 2021/0322749 A1 | 10/2021 | Rothenberg et al. | |
| 2021/0322750 A1 | 10/2021 | Harandi et al. | |
| 2021/0322751 A1 | 10/2021 | Jiang et al. | |
| 2021/0322752 A1 | 10/2021 | Jiang et al. | |
| 2022/0226630 A1 | 7/2022 | Griffith et al. | |
| 2022/0273931 A1 | 9/2022 | Jiang et al. | |
| 2023/0241369 A1 | 8/2023 | Prasad et al. | |

* cited by examiner

UNIVERSAL CAPS INCLUDING INTERFERING PROTRUSIONS FOR INTERFERENCE ENGAGEMENT TO MEDICAL CONNECTORS

BACKGROUND OF THE INVENTION

Field of the Invention

The present disclosure relates generally to caps for medical connectors and, in particular, to a medical cap configured to be attached to at least two different types of connectors, such as to a male luer connector or a female luer connector.

Description of Related Art

Vascular access devices (VADs) are commonly used medical devices, which can include intravenous (IV) catheters, such as peripheral catheters or central venous catheters. If not properly maintained or if exposed to a non-sterile environment, the VADs can become contaminated, sealed with blood clots, and/or can spread infection. Further, bacteria and other microorganisms may enter into a patient's vascular system from access hubs, ports, or valves upon connection to the VAD to deliver a fluid or pharmaceutical to a patient. Therefore, each access hub (or port/valve or connection) configured for attachment to a VAD is associated with some risk of transmitting a catheter related bloodstream infection (CRBSI) to a patient.

Many medical facilities implement sterile practices and protocols to ensure that VADs and access hubs or ports are used properly and do not become sealed or infected. These protocols often include sterilizing the access hubs, ports, and VADs, as well as flushing the catheter with a flush solution prior to use. Specifically, VAD standards of practice usually recommend flush procedures be performed after catheter placement, before fluid infusion, and before and after drug administration, blood sampling, transfusions, and/or administration of parenteral nutrition. Standards of practice can also require that access hubs, ports, and valves be capped with disinfection caps when not in use, to prevent microbial ingress into the hub, port, or valve and to sterilize areas of the hub, port, or valve that contact the VAD. Disinfection caps are disposable cap devices that contain an amount of cleaning or disinfecting solution for sterilizing portions of the port, hub, and valve.

Access hubs and ports can have a variety of different types of male or female connectors for securing the hub or port to the VAD. Currently, practitioners often carry several types of caps with them so that they can cap the different types of hubs and ports that may be used for a particular patient. For example, caps for male needleless connectors and female needleless connectors, as well as intravenous (IV) and hemodialysis lines, use different connector designs and may require different caps. In some examples, there can be "male disinfecting cap devices" for disinfecting ISO594-2 type of female threaded fluid luer connectors and "female disinfecting cap devices" for disinfecting ISO594-2 type of male threaded fluid luer connectors.

Some examples of universal caps that fit on both male and female connectors are known. For example, U.S. Pat. No. 10,871,246, entitled "Universal Connector or Cap for Male and Female Threaded Fittings," which is incorporated herein by reference in its entirety, discloses a cap including a threaded protrusion that can engage both a male connector and a female connector. However, there is a need for simpler cap designs that can be manufactured inexpensively and efficiently. The universal caps of the present disclosure are configured to attach to both male and female medical connectors in a secure manner sufficient for preventing microbial ingress. Further, the universal caps of the present disclosure are configured to be easy to manufacture in a single-molding process.

SUMMARY OF THE INVENTION

According to an aspect of the disclosure, a cap configured to engage at least a first connector and a second connector of different types includes a housing having a first end, an open second end, a sidewall extending between the first end and the second end, and a plurality of interfering protrusions extending inwardly from an inner surface of the sidewall configured to provide an interference engagement with the first connector or the second connector. The cap also includes an absorbent support positioned in the housing configured to contact portions of the first connector or the second connector, when the first connector or the second connecter is inserted into the housing, and a seal mounted to a portion of the absorbent support configured to cover an opening of the first connector or the second connector when the first connector or the second connector is inserted into the housing.

According to another aspect of the disclosure, a method for making a universal cap configured to engage at least a first connector and a second connector of different types includes a step of molding a housing of a universal cap, as a single molding process that produces an integrally formed housing. The molded housing includes a first end covered by a first end wall, an open second end, a sidewall extending between the first end and the second end, and a plurality of interfering protrusions extending inwardly from an inner surface of the sidewall configured to provide an interference engagement with the first connector or the second connector. The method also includes a step of inserting an absorbent support through the open second end of the housing such that the absorbent support is seated against the first end wall of the housing, and a step of inserting a seal against an end of the absorbent support.

In accordance with an embodiment of the present invention, a cap is configured to engage at least a first connector and a second connector of different types, the cap including a housing having a first end, an open second end, a sidewall extending between the first end and the second end, and a plurality of interfering protrusions extending inwardly from an inner surface of the sidewall configured to provide an interference engagement with the first connector or the second connector. The cap also includes an absorbent support positioned in the housing configured to contact portions of the first connector or the second connector, when the first connector or the second connecter is inserted into the housing; and a seal mounted to a portion of the absorbent support configured to cover an opening of the first connector or the second connector when the first connector or the second connector is inserted into the housing.

In accordance with an embodiment of the present invention, the cap is configured to be secured to the second connector by the interference engagement between the interfering protrusions and the second connector.

In accordance with an embodiment of the present invention, when the first connector is inserted into the housing, the plurality of interfering protrusions do not engage the first connector.

In accordance with an embodiment of the present invention, the housing further includes threads on the inner surface of the sidewall, and wherein the first connector is connected to the cap by an engagement between the threads of the housing and corresponding protrusions or grooves on the first connector.

In accordance with an embodiment of the present invention, the protrusions or grooves on the first connector include threads that engage the threads on the inner surface of the sidewall of the housing.

In accordance with an embodiment of the present invention, the first connector is a female luer connector.

In accordance with an embodiment of the present invention, the housing is sized to receive the female luer connector having a maximum outer diameter of at least 9.0 mm.

In accordance with an embodiment of the present invention, a threaded portion of the female luer connector has an outer diameter of less than 10.0 mm.

In accordance with an embodiment of the present invention, the plurality of interfering protrusions includes a plurality of crushable ribs extending over the inner surface of the sidewall of the housing, the ribs being configured to be crushed by an outer surface of the second connector, thereby forming the interference engagement between the second connector and the cap.

In accordance with an embodiment of the present invention, the plurality of crushable ribs extends substantially parallel to a longitudinal axis of the housing.

In accordance with an embodiment of the present invention, the plurality of crushable ribs is spaced about a circumference of the inner surface of the housing.

In accordance with an embodiment of the present invention, the plurality of crushable ribs is equidistantly spaced about a circumference of the inner surface of the housing.

In accordance with an embodiment of the present invention, the plurality of crushable ribs includes a rounded surface curving about a longitudinal axis of the rib.

In accordance with an embodiment of the present invention, the plurality of interfering protrusions includes (i) a first group of the plurality of interfering protrusions in a first tier of the housing having a first inner diameter, and (ii) a second group of the plurality of interfering protrusions in a second tier of the housing having a second inner diameter different from the first inner diameter.

In accordance with an embodiment of the present invention, the first group of the plurality of interfering protrusions are spaced about the first tier of the housing and the second group of the plurality of interfering protrusions are spaced about the second tier of the housing.

In accordance with an embodiment of the present invention, the plurality of protrusions comprises crushable ribs extending substantially parallel to a longitudinal axis of the housing, and wherein the first group of the plurality of interfering protrusions are not axially aligned with the second group of the plurality of interfering protrusions.

In accordance with an embodiment of the present invention, the second connector includes a male luer connector having a stem configured to be inserted into the absorbent support, such that the opening of the male luer connector is sealed by the seal mounted to the absorbent support, and the plurality of interfering protrusions form the interference engagement with a portion of the male luer connector.

In accordance with an embodiment of the present invention, the male luer connector further includes an annular shield comprising a threaded inner surface extending about the stem.

In accordance with an embodiment of the present invention, the housing is sized to receive the male luer connector having an outer diameter of from 8.0 mm to 14.0 mm.

In accordance with an embodiment of the present invention, the sidewall of the housing having a flexible portion proximate to the second end of the housing configured to press against and deform to accommodate portions of the first connector or the second connector when the first connector or the second connector is inserted into the housing.

In accordance with an embodiment of the present invention, the flexible portion of the sidewall has a variable inner diameter that is widest at the second end of the housing and becomes narrower towards the first end of the housing.

In accordance with an embodiment of the present invention, the flexible portion includes a plurality of tiers having different inner diameters.

In accordance with an embodiment of the present invention, the flexible portion of the sidewall is configured to extend radially outwardly to accommodate portions of the first connector or the second connector having an outer diameter larger than an inner diameter of the sidewall in an unbiased state.

In accordance with an embodiment of the present invention, the sidewall further includes a rigid portion that does not deform when the first connector or the second connector is inserted into the housing.

In accordance with an embodiment of the present invention, the rigid portion includes a threaded inner surface configured to engage a corresponding threaded outer surface of the first connector, and a plurality of outward protrusions extending outwardly from an outer surface of the sidewall for increasing rigidity of the rigid portion.

In accordance with an embodiment of the present invention, the rigid portion includes areas of increasing wall thickness and/or that are co-molded with a polymer that is more rigid than a material that forms other areas of the housing.

In accordance with an embodiment of the present invention, the housing is a single-molded part.

In accordance with an embodiment of the present invention, the housing includes a rigid thermoplastic polymer, such as polyester, polycarbonate, polypropylene, polyethylene, polyethylene terephthalate, or acrylonitrile butadiene styrene.

In accordance with an embodiment of the present invention, the absorbent support includes a cylindrical member sized to be received within a substantially cylindrical cavity defined by a portion of the inner surface of the sidewall of the housing.

In accordance with an embodiment of the present invention, the absorbent support includes a porous foam having a thermoplastic elastomeric material.

In accordance with an embodiment of the present invention, insertion of the first connector or the second connector into the cap causes the connector to contact the absorbent support, and wherein contact between the connector and the absorbent support mechanically removes objects from an outer surface of the connector.

In accordance with an embodiment of the present invention, the cap further includes a cleaning or disinfecting solution absorbed by the absorbent support, wherein the seal is configured to prevent or restrict the cleaning or disinfecting solution from flowing from the absorbent support into a lumen of the first connector or the second connector engaged to the cap.

In accordance with an embodiment of the present invention, the cleaning or disinfecting solution includes an antimicrobial, anti-fungal, antibacterial, or antiviral composition.

In accordance with an embodiment of the present invention, the cleaning or disinfecting solution includes about 0.5% to about 3.5% chlorhexidine gluconate, about 60% to 85% isopropyl alcohol (IPA), or combinations thereof.

In accordance with an embodiment of the present invention, the seal includes a closed cell foam.

In accordance with an embodiment of the present invention, a removable protective cover is attached to the open second end of the housing for protecting an interior of the housing and the absorbent support prior to use.

In accordance with an embodiment of the present invention, the protective cover includes a film with adhesive on a first side of the film for removably mounting the first side of the film to the open second end of the housing.

In accordance with an embodiment of the present invention, the protective cover is substantially impervious to air to prevent the absorbent support from drying prior to use.

In accordance with an embodiment of the present invention, the protective cover is connected to the open second end of the housing by heat sealing.

In accordance with an embodiment of the present invention, the absorbent support is shaped to clean and/or disinfect a distal portion and outer surface of a female connector, a tip and outer surface of a stem, and inner surface of an annular shield of a male connector.

In accordance with an embodiment of the present invention, the absorbent support includes a cavity extending axially inwardly from a second end surface of the absorbent support and wherein the seal is received within the cavity.

In accordance with an embodiment of the present invention, the housing includes a first tier having a first inner diameter, a second tier having a second inner diameter larger than the first inner diameter adjacent to the first flexible tier, and a third tier between the second tier and the open second end of the housing having a third inner diameter, which is larger than the first inner diameter or the second inner diameter.

In accordance with an embodiment of the present invention, the plurality of interfering protrusions are positioned on the first tier and/or the second tier of the housing, and the third tier does not include the interfering protrusions.

In accordance with an embodiment of the present invention, the housing further includes a threaded rigid portion between the first tier and the first end of the housing.

In accordance with an embodiment of the present invention, the threaded rigid portion includes threads extending inwardly from the inner surface of the sidewall, configured to engage corresponding threads of the first connector.

In accordance with an embodiment of the present invention, the threaded rigid portion further includes outward protrusions extending outwardly from an outer surface of the sidewall for increasing rigidity of the sidewall.

In accordance with an embodiment of the present invention, the first end of the housing is closed including a wall extending over the sidewall of the housing.

In accordance with an embodiment of the present invention, a method for making a universal cap configured to engage at least a first connector and a second connector of different types includes molding a housing of a universal cap as a single molding process that produces an integrally formed housing, wherein the housing comprises a first end covered by a first end wall, an open second end, a sidewall extending between the first end and the second end, and a plurality of interfering protrusions extending inwardly from an inner surface of the sidewall configured to provide an interference engagement with the first connector or the second connector; inserting an absorbent support through the open second end of the housing such that the absorbent support is seated against the first end wall of the housing; and inserting a seal against an end of the absorbent support.

In accordance with an embodiment of the present invention, the universal cap is configured to be secured to the second connector by the interference engagement between the interfering protrusions and the second connector, and wherein, when the first connector is inserted into the housing, the plurality of interfering protrusions do not engage the first connector.

In accordance with an embodiment of the present invention, the plurality of interfering protrusions includes a plurality of crushable ribs extending over the inner surface of the sidewall of the housing, the crushable ribs being configured to be crushed by an outer surface of the second connector, thereby forming the interference engagement between the second connector and the cap.

In accordance with an embodiment of the present invention, wherein the housing is formed by injection molding.

In accordance with an embodiment of the present invention, wherein molding the housing includes depositing a flowable polymer precursor into a mold and curing the polymer precursor to form a rigid thermoplastic polymer, such as polyester, polycarbonate, polypropylene, polyethylene, polyethylene terephthalate, or acrylonitrile butadiene styrene.

In accordance with an embodiment of the present invention, the absorbent support includes a cylindrical member sized to be received within a substantially cylindrical cavity defined by a portion of the inner surface of the sidewall of the housing.

In accordance with an embodiment of the present invention, wherein the method further includes soaking the absorbent support with a cleaning or disinfecting solution, such as an antimicrobial, anti-fungal, antibacterial, or antiviral composition.

In accordance with an embodiment of the present invention, wherein the cleaning or disinfecting solution includes about 0.5% to about 3.5% chlorhexidine gluconate, about 60% to 85% isopropyl alcohol (IPA), or combinations thereof.

In accordance with an embodiment of the present invention, the method further includes attaching a removable protective cover over the open second end of the housing.

In accordance with an embodiment of the present invention, wherein the protective cover includes a film with adhesive on a first side of the film for removably mounting the first side of the film to the open second end of the housing.

In accordance with an embodiment of the present invention, wherein the protective cover is attached to the housing by heat sealing.

DESCRIPTION OF THE INVENTION

Figure 1B:
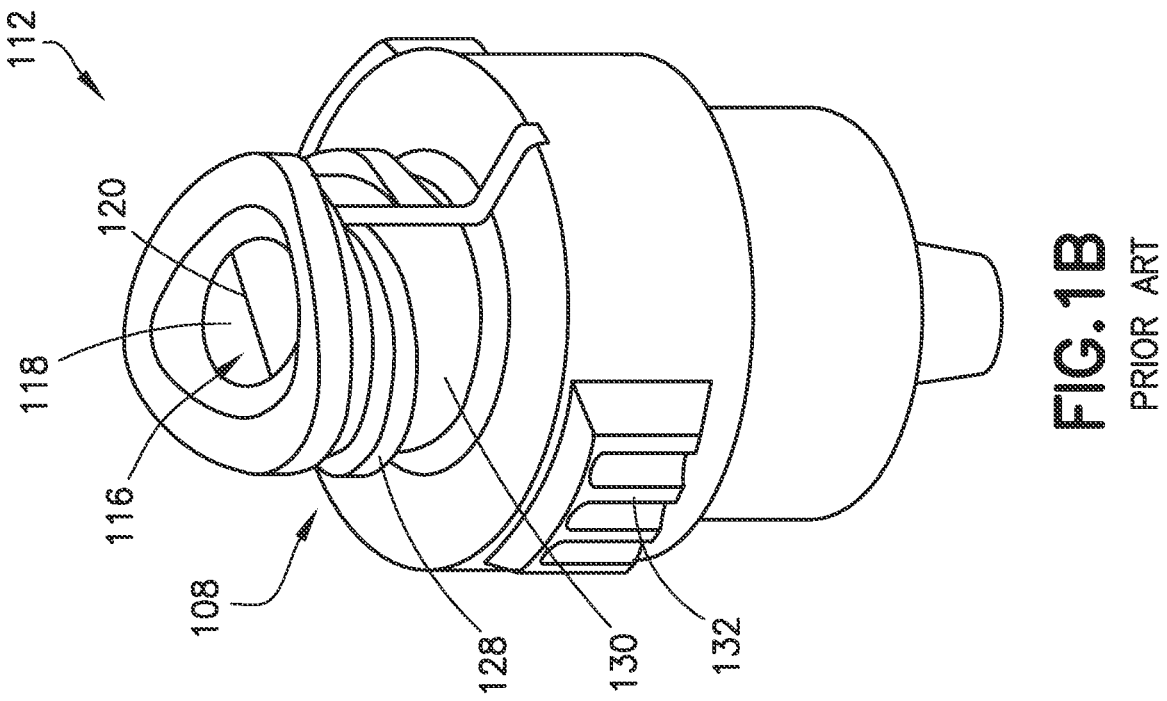
FIG. 1B is an example of a female connector including a septum with a slit, as is known in the prior art.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

The present disclosure is directed to a cap 10 configured to be connected to a medical connector 110, 112, such as an access hub, port, or valve for a VAD, to prevent the connector, port, or VAD from being contaminated by, for example, microbes, debris, or other contaminants. In some examples, the cap 10 can be configured to clean or disinfect the connector 110, 112 or port, ensuring that the connector 110, 112 or port remains sterile prior to use. The cap 10 can be configured to remain in place on a connector 110, 112 or port for at least seven days, which is a maximum time of recommended use permitted by many medical facility sterile practice guidelines. The cap 10 can be configured to engage or be connected to different sizes, configurations, or types of medical connectors 110, 112. For example, the cap 10 can be configured to engage or be connected to both a male connector 110 and a female connector 112.

Male and Female Luer Connectors

Figure 1A:
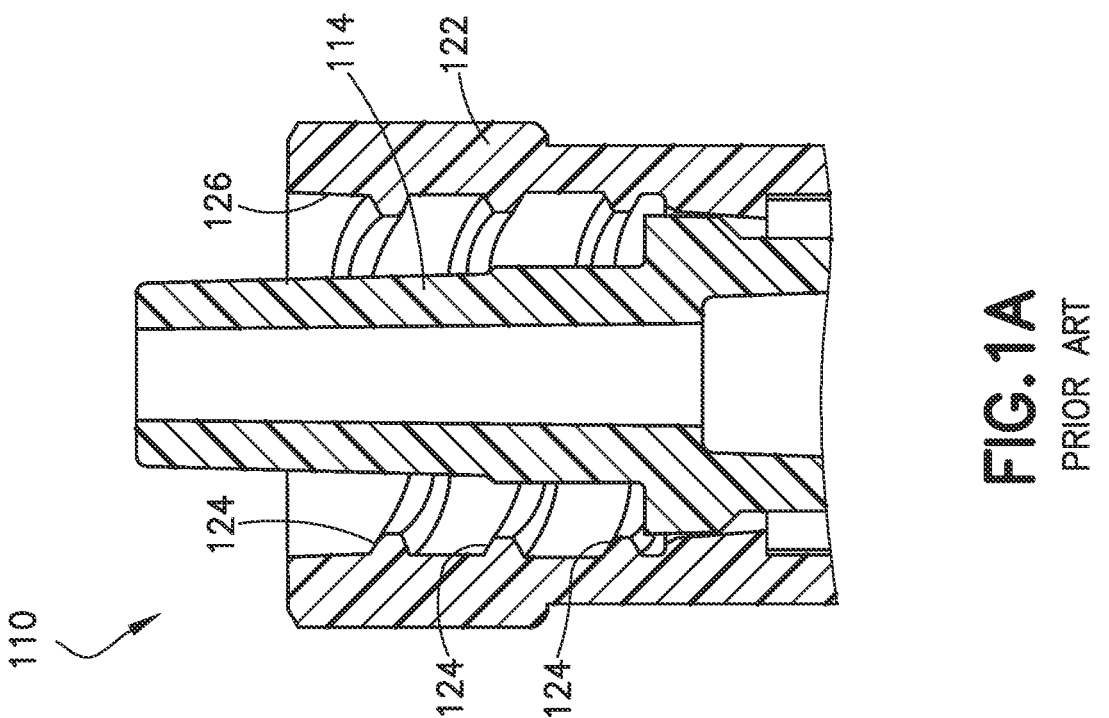
FIG. 1A is a cross-sectional view of an exemplary male connector, as is known in the prior art.

As used herein, a "male connector" refers to a connector 110 comprising an elongated member, such as a tubular member or stem 114, configured to be inserted in a tube or opening having an inner diameter that is larger than an outermost diameter of the male connector 110. An exemplary male connector 110 is shown in FIG. 1A. A "female connector" refers to a connector 112 comprising an opening or port 116 that is configured to receive an elongated member or tubular member of another object or device in order to connect the object or device to the female connector 112. The female connector 112 can have a cover or septum 118 over the opening 116. An exemplary female connector 112 including a septum 118 with a slit 120 is shown in FIG. 1B.

In some examples, the cap 10 of the present disclosure is configured to engage both a male luer connector 110 and a female luer connector 112. For example, the cap 10 can be configured to receive a female luer connector 112 having an outer diameter of at least 9.0 mm, at least 10.0 mm, or at least 12.5 mm. The cap 10 can also be sized to receive a male luer connector 110 having an outer diameter of from about 8.0 mm to about 14.0 mm.

As used herein, a "luer connector" refers to a connector that includes a tapered portion (i.e., a luer taper) for creating a friction engagement between a tapered stem 114 or elongated member of a male luer connector 110 and a tapered cavity. Specifically, the male luer connector 110 can include a tapered stem 114 or elongated member having a tapered outer surface. The female luer connector 112 can include a tapered cavity configured to receive and engage the tapered stem 114 or elongated member to connect the male luer connector 110 to the female luer connector 112.

In order to secure the male and female connectors 110, 112 together, in some examples, the connectors 110, 112 can include engaging structures, such as threads, for drawing the connectors 110, 112 together. For example, as shown in FIG. 1A, the male luer connector 110 can include an annular shield 122 extending about the tapered stem 114 or elongated member. The annular shield 122 can include threads 124 on an inner surface 126 of the shield 122 configured to engage corresponding threads 128 on an outer surface 130 of the female luer connector 112. As shown in FIG. 1B, the female luer connector 112 can include threads 128 extending from the outer surface 130 positioned to engage the threads 124 on the inner surface 126 of the annular shield 122 of the male luer connector 110. Twisting the female connector 112 relative to the male connector 110 causes the corresponding threads 124, 128 to engage, which draws the connectors 110, 112 together, such that the tapered stem 114 or elongated member of the male luer connector 110 moves through the opening 116 of the female connector 112. In some examples, the female connector 112 can also include vertical ridges 132 near a proximal end of the female connector 112, which can be used to manipulate the female connector 112 making it easier to twist the female connector 112 compared to another connector or device. As previously described, the caps 10 of the present disclosure are configured to cover both the male luer connector 110 (shown in FIG. 1A) and the female luer connector 112 (shown in FIG. 1B).

Universal Caps for Male and Female Connectors

Figure 2B:
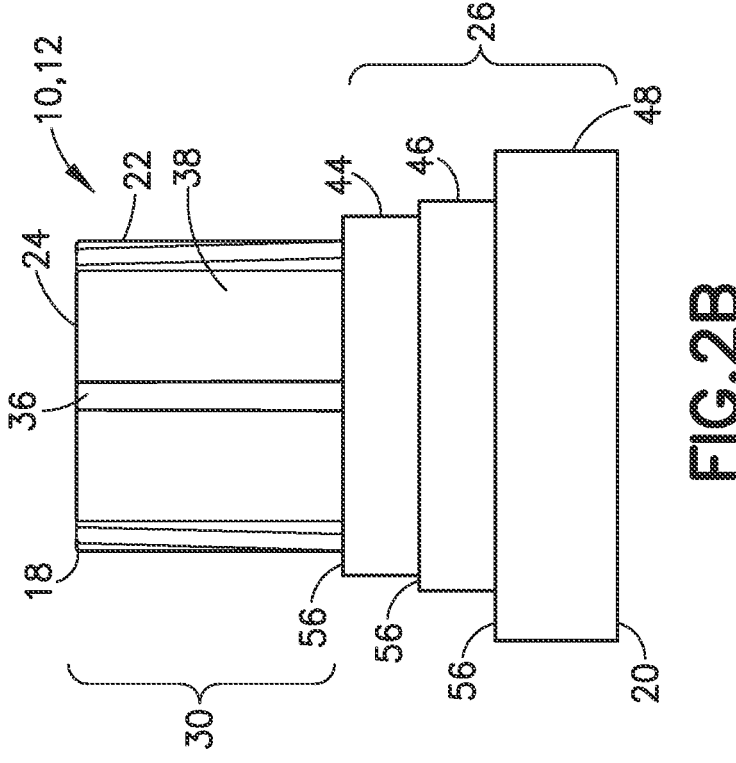
FIG. 2B is a front view of the universal cap of FIG. 2A.
Figure 2A:
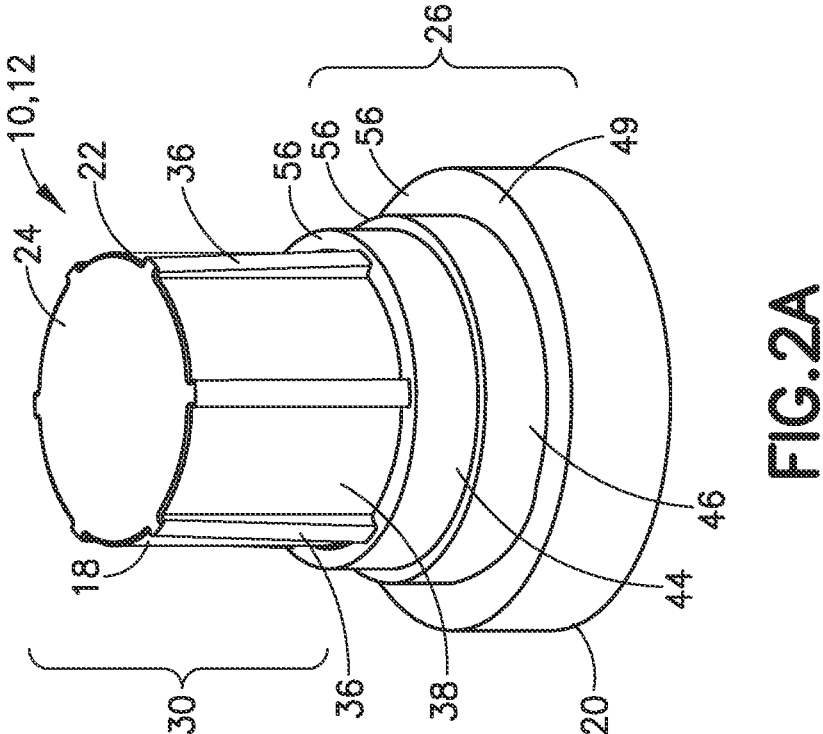
FIG. 2A is a perspective view of a universal cap for medical connectors, according to an aspect of the present disclosure.
Figure 2C:
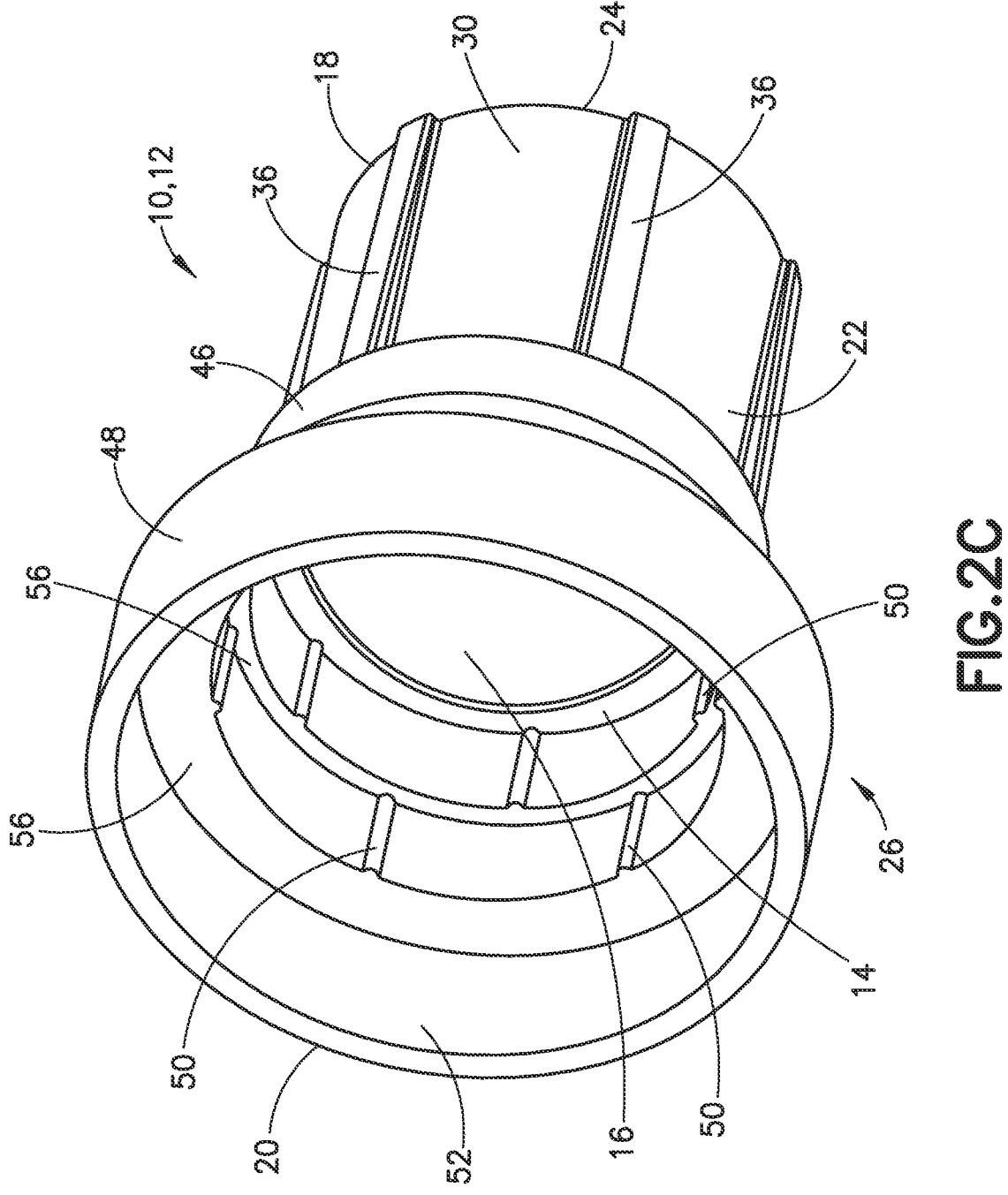
FIG. 2C is another perspective view of the universal cap of FIG. 2A showing the open end of the cap.
Figure 2D:
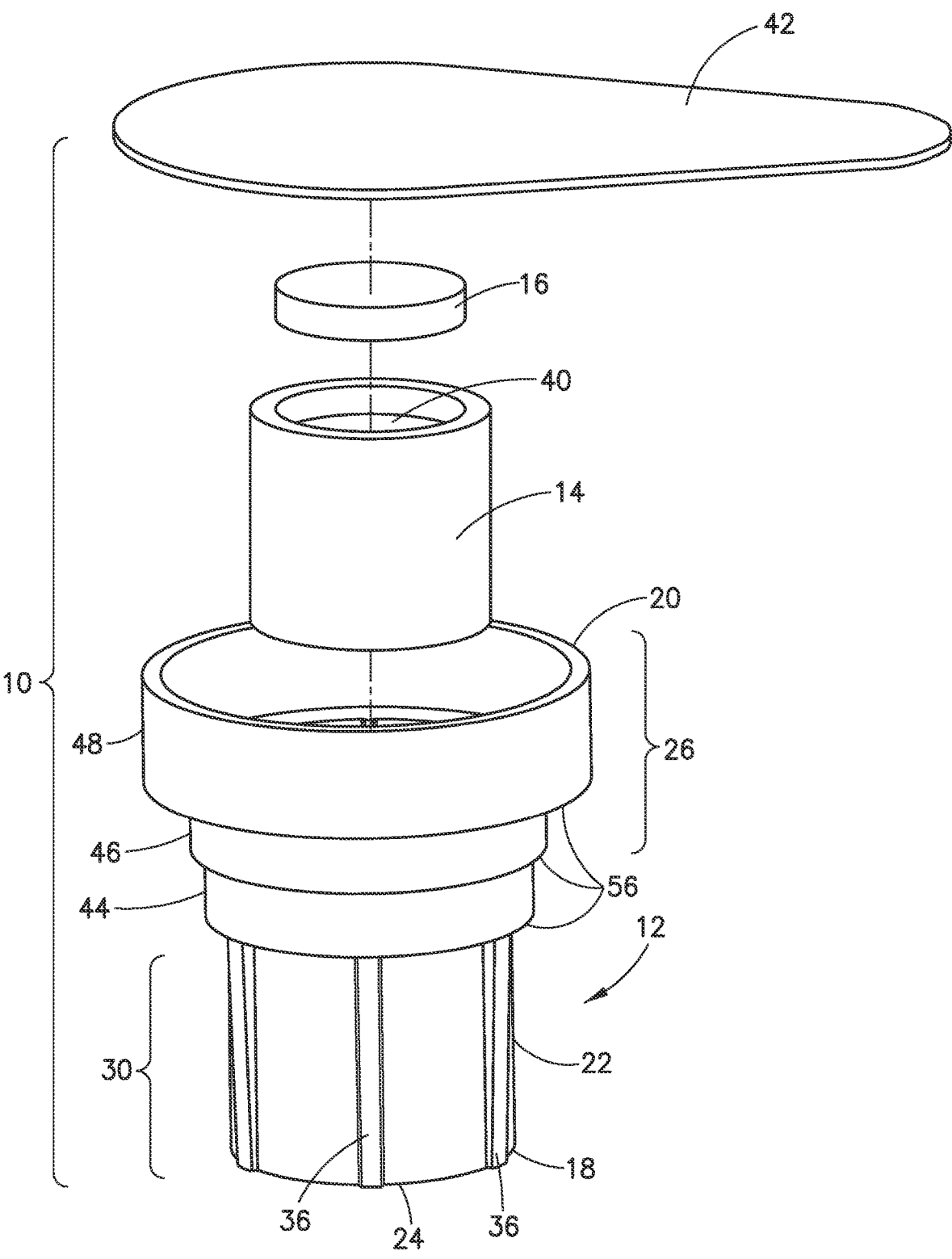
FIG. 2D is an exploded perspective view of the universal cap of FIG. 2A.
Figure 2E:
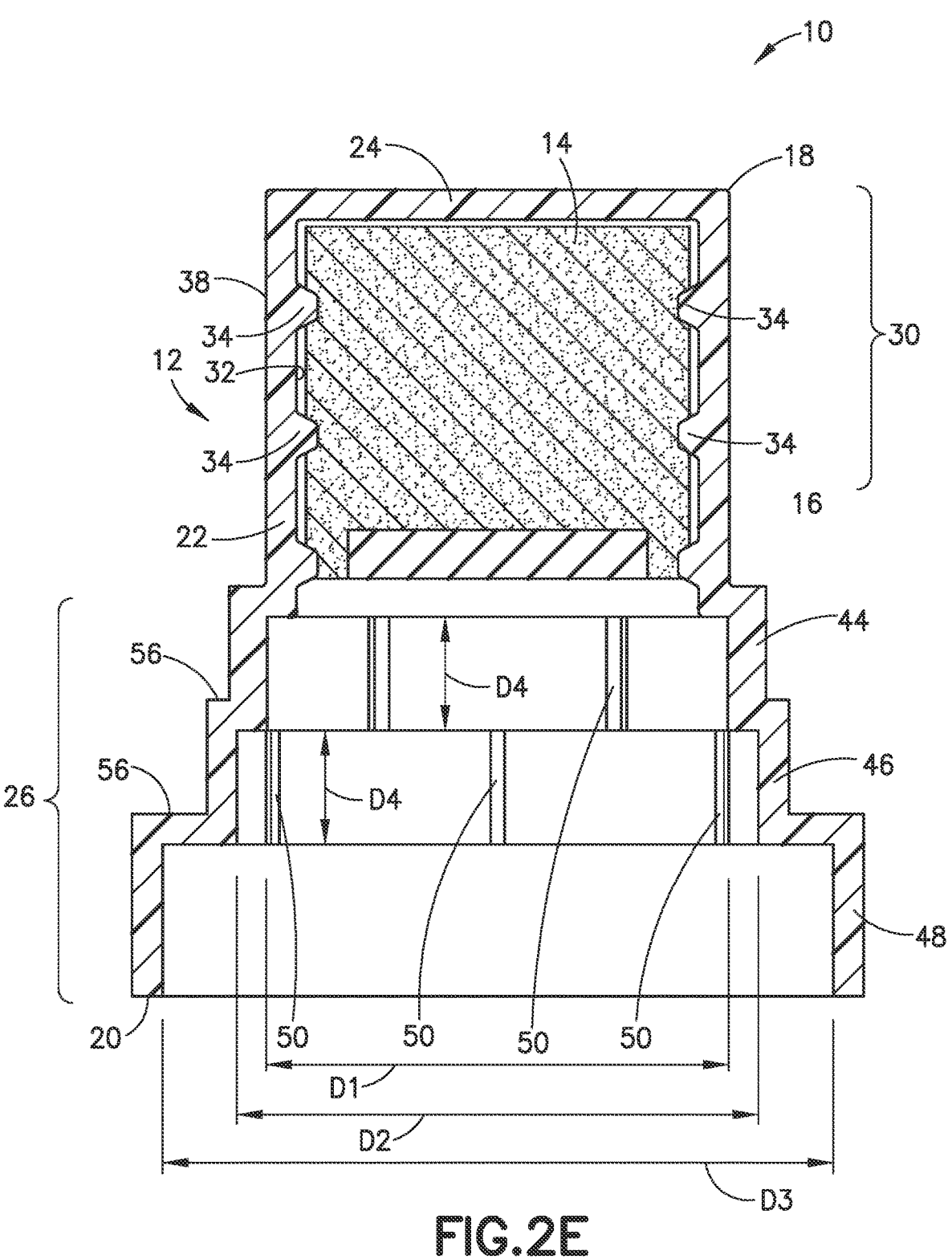
FIG. 2E is a cross-sectional view of the universal cap of FIG. 2A.

FIGS. 2A-2E show an exemplary universal cap 10 configured to be connected to different types of connectors, such as to both the male luer connector 110 and the female luer connector 112. Specifically, FIG. 2A is a perspective view of the cap 10. FIG. 2B is a front plan view of the cap 10. FIG. 2C is a perspective view of an open bottom end 20 of the cap 10. FIG. 2D is an exploded perspective view of the cap 10. FIG. 2E is a cross-sectional view of the cap 10.

As shown in FIGS. 2A-2E, the cap 10 comprises a housing 12 comprising a first or top end 18, an open second or bottom end 20, and a sidewall 22 extending between the top end 18 and the bottom end 20. The top end 18 of the cap 10 can be open or can comprise a top end wall 24 extending over the top end 18 of the housing 12.

The cap 10 further comprises an absorbent support 14 positioned in the housing 12 configured to contact portions of the male connector 110 or the female connector 112 inserted into the housing 12. For example, the cap 10 can be configured such that when attached to the male luer connector 110, the stem 114 or elongated member of a male luer connector 110 inserts into and forms an interference engagement with the absorbent support 14. A bottom portion of the housing 12 can also engage a corresponding portion of the male luer connector 110 to form an additional interference engagement between the housing 12 and the connector 110. For example, the housing 12 can comprise one or multiple interfering protrusions 50 extending inwardly from an inner surface 52 of a sidewall 22 of the housing 12. The interfering protrusions 50 can be configured to provide or enhance the interference engagement between the cap 10 and portions of the connectors 110, 112.

The cap 10 further comprises a seal 16 mounted to a portion of the absorbent support 14 configured to cover an opening or lumen of the male connector 110 or the female connector 112, when the male connector 110 or the female connector 112 is inserted into the housing 12. For example, when the male luer connector 110 is inserted in the housing 12, the seal 16 can contact and cover an opening at a distal end of the stem 114 or elongated member of the male luer connector 110, which seals the male luer connector 110. The seal 16 can prevent fluids, such as cleaning or disinfecting solution in the cap 10, from flowing into the lumen of the male connector 110.

The cap 10 is configured to engage a variety of different configurations and orientations of medical connectors 110, 112. For example, the cap 10 can be configured to be secured to the female connector 112 by either an interference engagement or a threaded engagement between the inner surface 52 of the housing 12 and a portion of the female connector 112. The cap 10 can also be configured to be secured to the male connector 110 by the interference or friction engagement between the outer surface 130 of the male connector 110 and the interfering protrusions 50 and/or the absorbent support 14.

There are numerous different commercially available medical devices, such as hubs, ports, and valves, which can include different variations of male or female connectors 110, 112. The cap 10 of the present disclosure is configured to adapt or deform so that it can be secured to numerous different types and sizes of connectors. For example, the caps 10 of the present disclosure can be configured to attach to male or female Luer-Lok™ connectors by Becton Dickinson and Company. The caps 10 of the present disclosure can also be configured to cover different connector designs including, without limitation, the BD Q-Syte™, BD MaxZero™, BD MaxPlus™, and SmartSite™ needle free connectors by Becton Dickinson and Company. The caps 10 can also be configured to be connected to male and/or female connectors by other manufactures including, without limitation, MicroClave® connectors (ICU Medical Inc.) and Ultrasite® connectors (B. Braun Medical Inc.). In other examples, the cap 10 can be configured to be connect to one or more of the following commercially available male connectors: Kendall 2001NP; BD MP5303-C; ICU Med 12664-28; RyMed RYM-5307HPU; B. Braun 470108; Baxter 2C8537; Kawasumi IV-0094; Zyno B2-70071-D; B. Braun 470124; Baxter 2C7462; and Smith's Medical 536035.

In some examples, the housing 12 of the cap 10 can be a molded part formed from a thermoplastic material, such as polyester, polycarbonate, polypropylene, polyethylene, polyethylene terephthalate, or acrylonitrile butadiene styrene. The material can be a durable material, such as a material having a shore hardness D value of less than or equal to 60 shore D. Alternatively, the cap 10 can be formed from a more flexible material, such as a material having a shore hardness A value less than or equal to 80 shore A. The housing 12 can be formed as a single integral and/or molded part. For example, the housing 12 can be formed by an injection molding process, where the entire housing 12 is formed in a single mold.

Figure 3A:
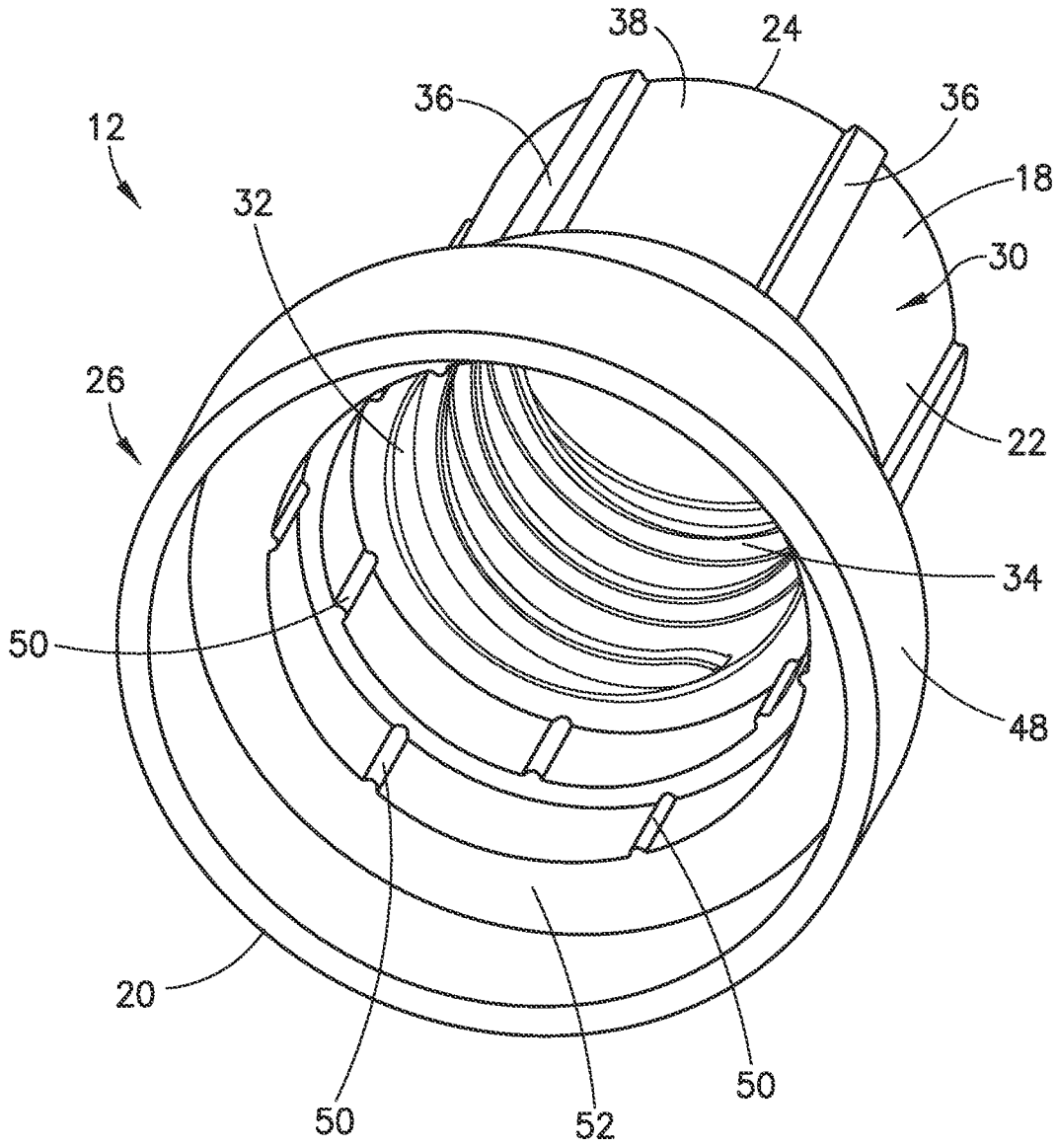
FIG. 3A is a perspective view of a housing of the cap of FIG. 2A, according to an aspect of the present disclosure.
Figure 3B:
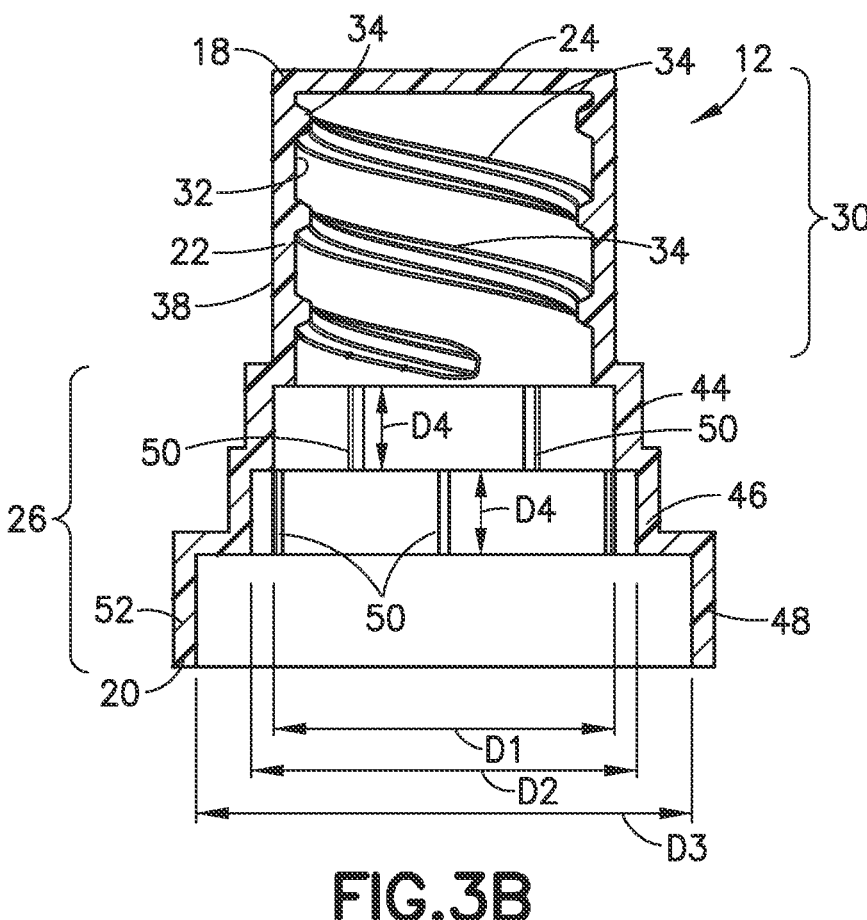
FIG. 3B is a cross-sectional view of the housing of FIG. 3A.
Figure 3C:
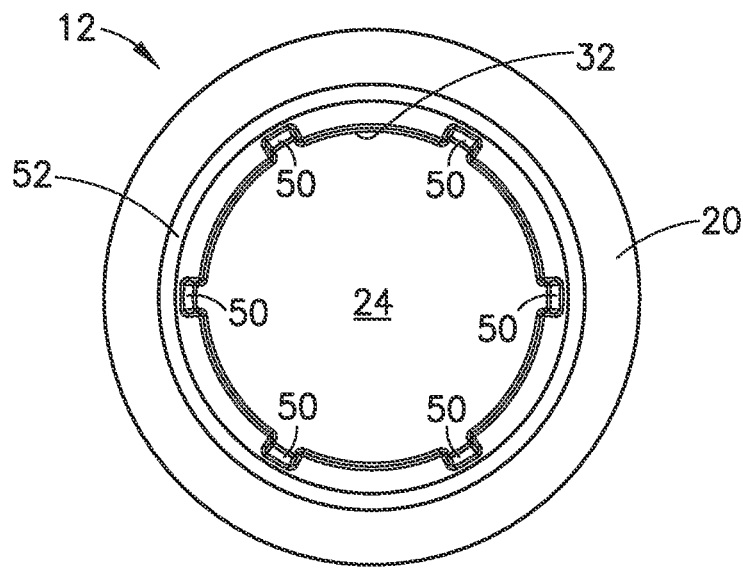
FIG. 3C is a bottom plan view of the housing of FIG. 3A.

As shown in FIGS. 2A-2E, as well as in FIGS. 3A-3C, in some examples, the sidewall 22 of the housing 12 includes a flexible portion 26 proximate to the bottom end 20 of the housing 12 configured to press against and deform to accommodate portions of the female connector 112 or the male connector 110 when the connector 110, 112 is inserted into the housing 12. The flexible portion 26 of the sidewall 22 can be configured to extend radially outwardly to accommodate portions of the connectors 110, 112 having an outer diameter larger than an inner diameter of the sidewall 22 of the housing 12 in an unbiased state. As used herein, an "unbiased state" refers to an orientation of the cap 10 when no external forces are applied to the cap 10 and when the cap 10 is not connected to a connector device or port. The flexible portion 26 can also be configured to bend, compress, or deform to adopt a curvature of a distal end portion of the connector 110, 112, hub, or port, such that the bottom end 20 of the cap 10 becomes curved when inserted onto the connector 110, 112, hub, or port. Further, the flexible portion 26 of the sidewall 22 can be configured to deform to form the friction engagement or interference engagement with the male connector 110 to secure the cap 10 to the male connector 110.

As previously described, the housing 12 can be made in a single molding process meaning that the flexible portion 26 of the housing 12 can be formed from the same material as other more rigid areas of the housing 12. In that case, the flexible portion 26 of the housing 12 can be molded to be thinner than other areas of the housing 12, thereby providing the flexible portion 26 with sufficient flexibility to deform and conform to a shape of and/or to engage the connector 110, 112, hub, or port.

In some examples, the flexible portion 26 of the sidewall 22 has a variable inner diameter to accommodate connectors 110, 112 of different sizes. For example, the flexible portion 26 can be widest at the bottom end 20 of the housing 12 and can become narrower moving axially through the housing 12. In some examples, some portion or the entire flexible portion 26 can be tapered, having an inner cavity with an angled or frusto-conical surface. In other examples, the flexible portion 26 can be tiered, such that an inner diameter of the flexible portion 26 decreases moving axially through the housing 12, but in a non-continuous manner. For example, the flexible portion 26 of the sidewall 22 can include three tiers, each having different inner diameters, as shown in FIGS. 2A-3C. Each tier includes a substantially vertical wall and an annular horizontal tread 56.

More specifically, the tiered flexible portion 26 can comprise a narrowest or first tier 44 having a first inner diameter D1, positioned at a top of the flexible portion 26. The tiered flexible portion 26 further includes a middle or second tier 46 having a second inner diameter D2 and a third tier 48 having a third inner diameter D3. While not shown in FIGS. 2A-3C, one or more of the tiers 44, 46, 48 can have an annular tapered or angled surface. In some examples, the first, second, and third tiers 44, 46, 48 can be sized or configured to engage annular shields 122 (shown in FIG. 1A) or other portions of different commercially available male connectors 110 or female connectors 112. For example, the different tiers of the flexible portion 26 can have an inner diameter D1, D2 that matches an outer diameter of the annular shield 122 of the commercially available male connectors 110. Many commercially available male connectors 110 have an annular shield 122 with an outer diameter of either 9.1 mm to 9.4 mm or 10.3 mm to 10.4 mm. For example, male connectors 110 by RyMed, B. Braun, Zyno, and Smith's Medical often have an outer diameter of about 9.1 mm to 9.4 mm. By contrast, male connectors 110 by Kendall, Becton Dickinson, ICU Medicals, Baxter, and Kawasumi often have an outer diameter of about 10.4 mm.

Accordingly, the narrowest or first tier 44 can be adapted to form an interference engagement with an annular shield 122 having an outer diameter of about 9.1 mm to about 9.4 mm, meaning that the inner diameter D1 of the first tier 44 is about or slightly larger than 9.1 mm. The second tier 46 can be adapted to form an interference engagement with an annular shield 122 having an outer diameter of about 10.3 mm or 10.4 mm, meaning that the inner diameter D2 of the second tier 46 can be about or slightly larger than 10.3 mm. The third tier 48 can be adapted to form an interference engagement with a portion of a female connector, such as with portions of the BD Q-Syte™ connector by Becton Dickinson. In particular, the diameter D3 of the third tier 48 can be about 13.4 mm or about 13.5 mm to form an interference engagement with the vertical ridges 132 of the female connector 112 shown in FIG. 1B.

As previously described, the flexible portion 26 of the housing 12 further comprises the interfering protrusions 50 extending radially inwardly from the inner surface 52 of the sidewall 22. The interfering protrusions 50 can be configured to contact and form the interference engagement with the annular shields 122 of a male connector 110. The interfering protrusions 50 can be positioned such that they do not form an interference engagement with a female connector 112, when a female connector 112 is inserted into the cap 10. Instead, the female connector 112 can form an interference engagement or a threaded engagement with other portions of the housing 12. The interfering protrusions 50 can have a wide variety of shapes and configurations depending, for example, on how tightly the cap 10 should be engaged to the connector 110, 112. For example, the interfering protrusions 50 can comprise straight or curved ribs or ridges, detents, notches, annular flanges, or other structures protruding inwardly from the inner surface 52 of the sidewall 22.

In some examples, the interfering protrusions 50 are crushable ribs extending over the inner surface 52 of the sidewall 22 of the housing 12. As used herein, "crushable" means structures that are configured to be deformed (e.g., bent, pushed downward, folded, creased, broken, flattened, or otherwise modified in shape) when the connector 110 is pressed against the interfering protrusions 50 or ribs, which creates the interference engagement between the male connector 110 and the cap 10. As shown, for example, in FIGS. 2C, 2E, and 3A-3C, the crushable ribs can be elongated structures extending axially through the housing 12 along portions of the inner surface 52 of the sidewall 22. For example, the ribs can be parallel or substantially parallel (e.g., within about 15 degrees, 10 degrees, or 5 degrees of parallel) to a longitudinal axis of the housing 12. In some examples, the housing 12 includes multiple groups of the protrusions 50 or ribs. For example, the housing 12 can include a first group of ribs extending inwardly from an inner surface 52 of the first tier 44 of the housing 12 and a second group of ribs extending inwardly from an inner surface 52 of the second tier 46 of the housing 12. The first group of ribs can be configured to form an interference engagement with male connectors 110 with a narrow shield 122 (e.g., a shield 122 having an outer diameter of about 9.1 mm to about 9.4 mm). The second group of ribs (in the second tier 46) can be configured to form the interference engagement with a male connector 110 having a wider shield 122 (e.g., a shield 122 having an outer diameter of about 10.4 mm). The third tier 48, which can be sized to engage the vertical ridges 132 (shown in FIG. 1B) of the female connector 112 can be free from interfering protrusions 50 or crushable ribs.

The interfering protrusions 50 or ribs can be any suitable length determined, for example, based on dimensions of the tiers 44, 46, 48 and/or on how tightly the male connector 110 should fit into the cap 10. In some examples, the ribs have a length D4 (shown in FIG. 2E) of about 2.25 mm to about 2.50 mm. In order to provide a sufficient interference engagement with the connector 110, the ribs can protrude from the inner surface 52 of the sidewall 22 by a distance or height of about 0.1 mm to about 0.5 mm, or preferably about 0.3 mm, and can have a width of about 2.30 mm to about 2.50 mm. Further, in some examples, the ribs can have a rounded or chamfered surface curving about a longitudinal axis of each rib.

The interfering protrusions 50 or ribs can be spaced apart about a circumference of the tiers 44, 46. The ribs can be equidistantly spaced apart from one another or angular distances between the ribs can vary. As shown in FIG. 3C, the housing 12 can include six ribs in each tier 44, 46 of the housing 12 (i.e., twelve total ribs). In other examples, the tiers 44, 46 can include fewer than six ribs or more than six ribs. The six ribs of each tier 44, 46 can be spaced apart by about 60 degrees. Further, as shown in FIG. 2E, the ribs of different tiers 44, 46 may not be axially aligned and can be offset by an angular distance of, for example, about 15 degrees. Specifically, as shown in FIGS. 2E and 3C, ribs of the first tier 44 can be positioned at the 0 degree, 60 degree, 120 degree, 180 degree, 240 degree, and 300 degree positions about a circumference of the first tier 44. Ribs of the second tier 46 can be positioned at the 15 degree, 75 degree, 135 degree, 195 degree, 255 degree, and 315 degree positions about a circumference of the second tier 46.

In some examples, the sidewall 22 of the cap 10 also includes a rigid portion 30 that does not deform when the male connector 110 or the female connector 112 is inserted onto the housing 12. The rigid portion 30 can be a substantially cylindrical structure extending between the closed top end 18 of the housing 12 and the first tier 44 of the flexible portion 26 of the sidewall 22. The rigid portion 30 can be formed from the same material as the flexible portion 26. However, the rigid portion 30 can be thicker than the flexible portion 26 to resist deformation. In some examples, the rigid portion 30 includes an inner surface 32 with threads 34 configured to engage threads 128 on the outer surface 130 of the female connector 112. For example, the threads 34 can make one or more complete turns about the inner surface 32 of the rigid portion 30 depending about a height of the rigid portion 30. In some examples, as shown in FIGS. 2A-3E, the threads 34 can make at least two complete turns about the inner surface 32 of the rigid portion 30 in order to ensure that the cap 10 can be used with female connectors 112 of various heights. In other examples, the inner surface 32 of the rigid portion 30 can be smooth, without threads. In that case, the cap 10 can be configured to form an interference engagement between the inner surface 32 of the rigid portion 30 and the female connector 112.

In some examples, the rigid portion 30 further comprises outward protrusions, such as axial ridges 36, extending outwardly from an outer surface 38 of the sidewall 22 for providing rigidity for the rigid portion 30. The axial ridges 36 may also make the cap 10 easier to grip and manipulate for users. The axial ridges 36 can have a variety of different shapes. For example, the ridges 36 can be square or rectangular, having longitudinal edges extending a length of each ridge 36. In other examples, surfaces of the ridges 36 can be rounded, chamfered, or curved. As shown in FIG. 2A, the rigid portion 30 can include six axial ridges 36 positioned at the 0 degree, 60 degree, 120 degree, 180 degree, 240 degree, and 300 degree positions about a periphery of the rigid portion 30 of the cap 10. In other examples, the rigid portion 30 can include fewer than six axial ridges 36 or more than six axial ridges 36. Alternatively or in addition, the rigid portion 30 can include areas that are co-molded with a more rigid polymer to increase rigidity of the rigid portion 30.

With specific reference to FIGS. 2D and 2E, the absorbent support 14 of the cap 10 can be a cylindrical structure or member sized to be received within a substantially cylindrical cavity defined by the inner surface 32 of the rigid portion 30. The absorbent support 14 can be held within the cylindrical cavity by conventional adhesives or fasteners. In other examples, the absorbent support 14 can be held in place by friction between the inner surface 32 of the rigid portion 30 and the absorbent support 14.

In some examples, the absorbent support 14 can be formed from an absorbent material capable of absorbing a cleaning or disinfecting solution for cleaning and/or disinfecting portions of the male connector 110 and the female connector 112. In particular, the absorbent support 14 can be shaped and configured to clean and/or disinfect a distal or top portion of a female connector, including the septum 118 and slit 120 shown in FIG. 1B, as well as the outer surface 130 of the tubular portion of the female connector 112. The absorbent support 14 can also be shaped and configured to clean and/or disinfect the tip and sides of the stem 114, as well as the inner surface 126 and threads 124 of the annular shield 122 of the male connector 110 (shown in FIG. 1A).

In some examples, the material of the absorbent support 114 can be abrasive with sufficient texture, friction, and/or anti-slip properties to scrub surfaces of the connectors 110, 112 to mechanically remove microbes, debris, and other contaminants from surfaces of the connectors 110, 112. The absorbent support 14 may also have sufficient texture to create or enhance the interference engagement with the stem 114 or elongated member of the male connector 110 when the male connector 110 is inserted into the housing 12. The absorbent support 14 can comprise a thermoplastic elastomer, such as polypropylene, polyethylene, or synthetic or natural rubber (e.g., isoprene).

Figures 4A, 4B:
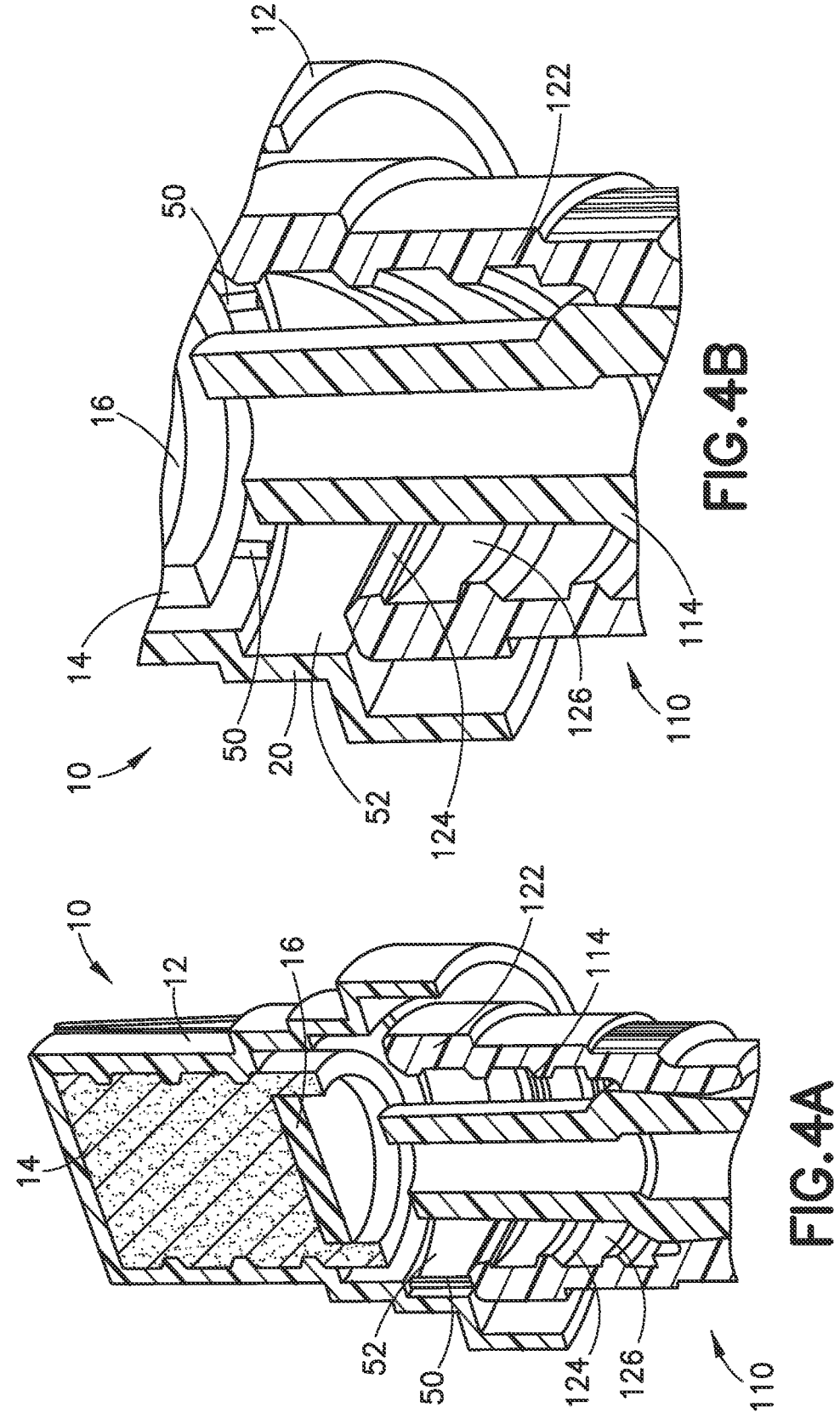
FIGS. 4A and 4B are perspective cross-sectional views showing a male luer connector inserted into the universal cap of FIG. 2A, according to an aspect of the present disclosure.
Figure 4C:
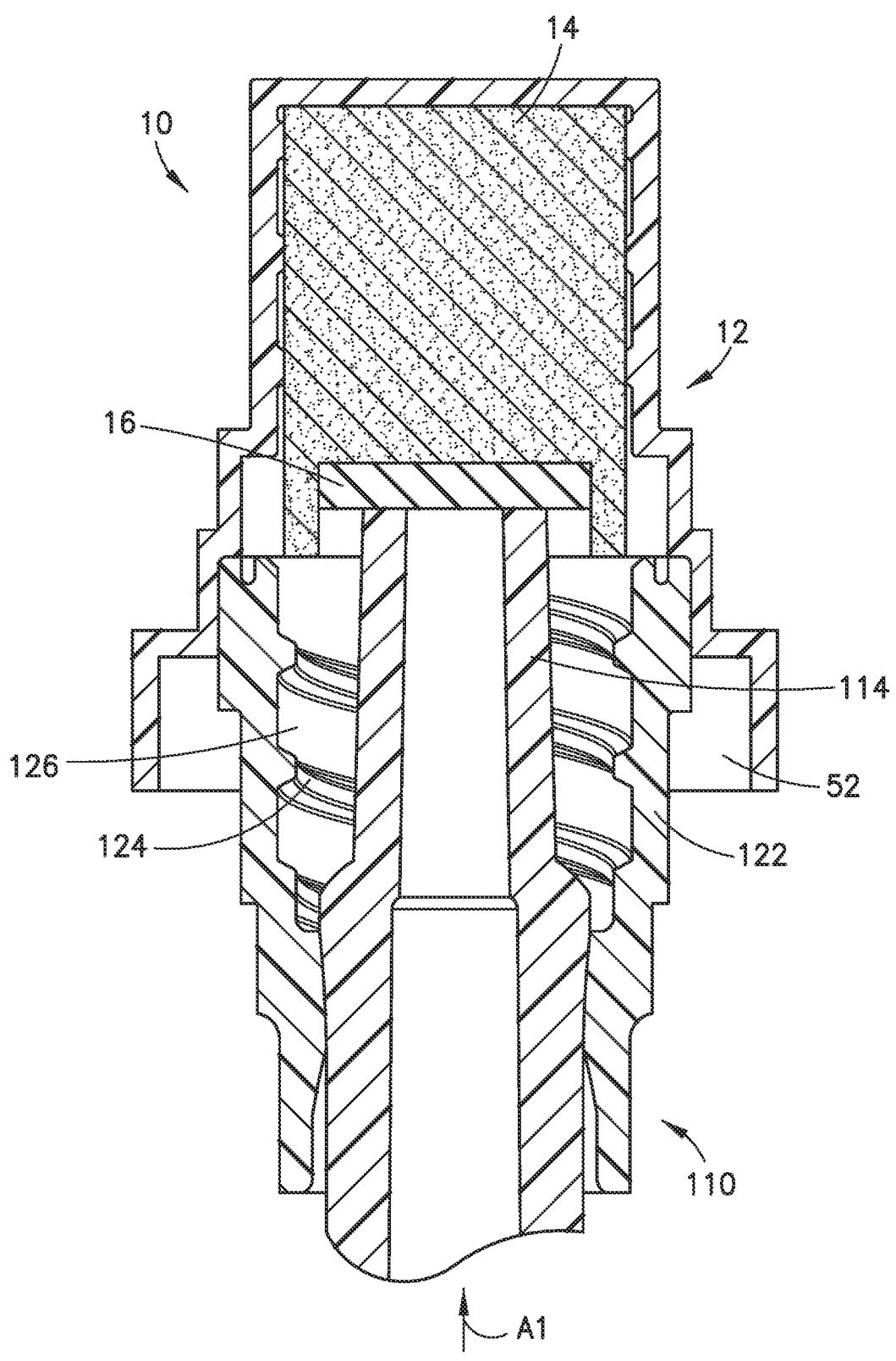
FIG. 4C is a front cross-sectional view of the universal cap connected to the male luer connector of FIGS. 4A and 4B.
Figure 4D:
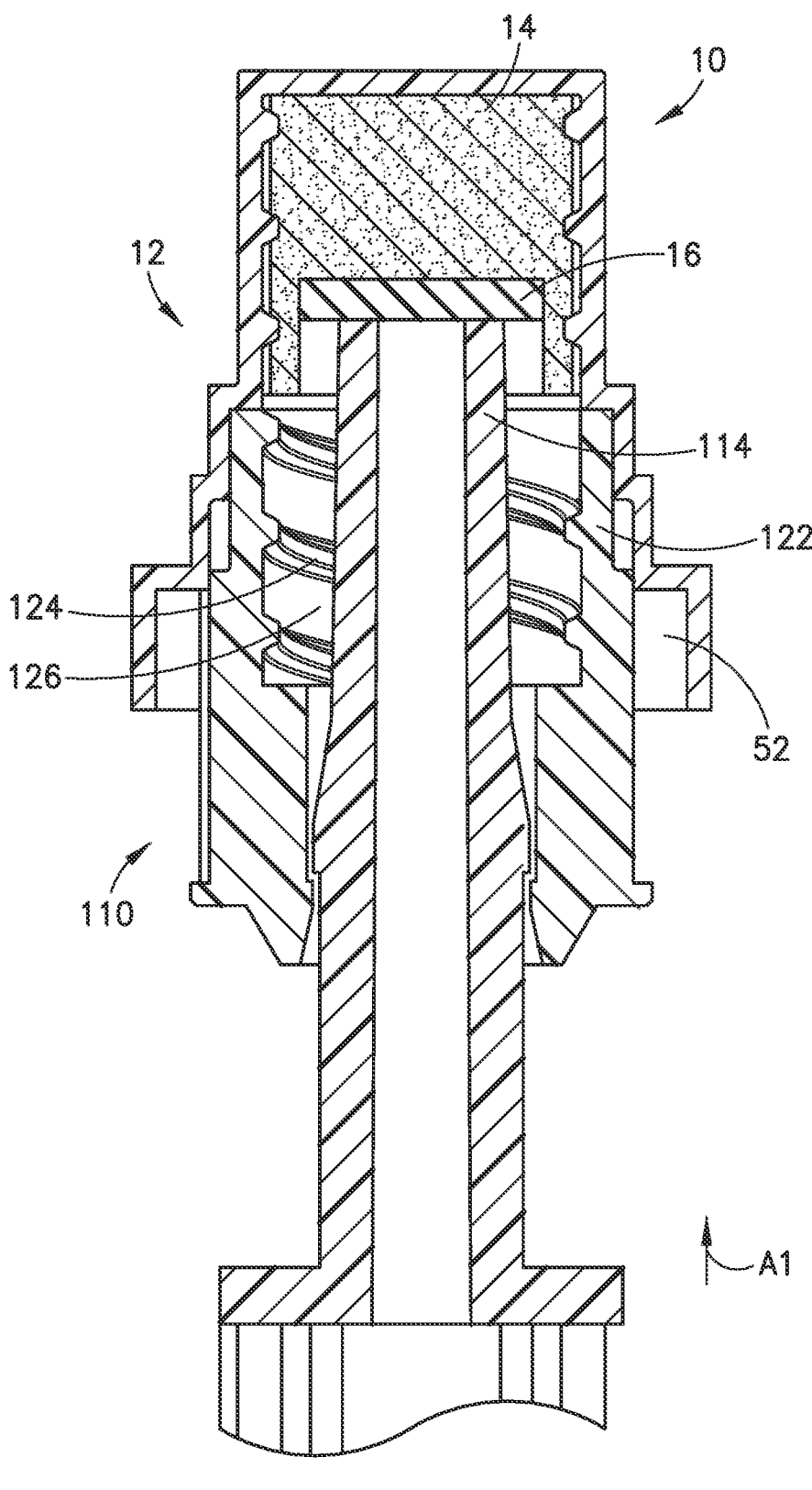
FIG. 4D is a front cross-sectional view of another exemplary male luer connector inserted into the universal cap of FIG. 2A, according to an aspect of the present disclosure.
Figure 5A:
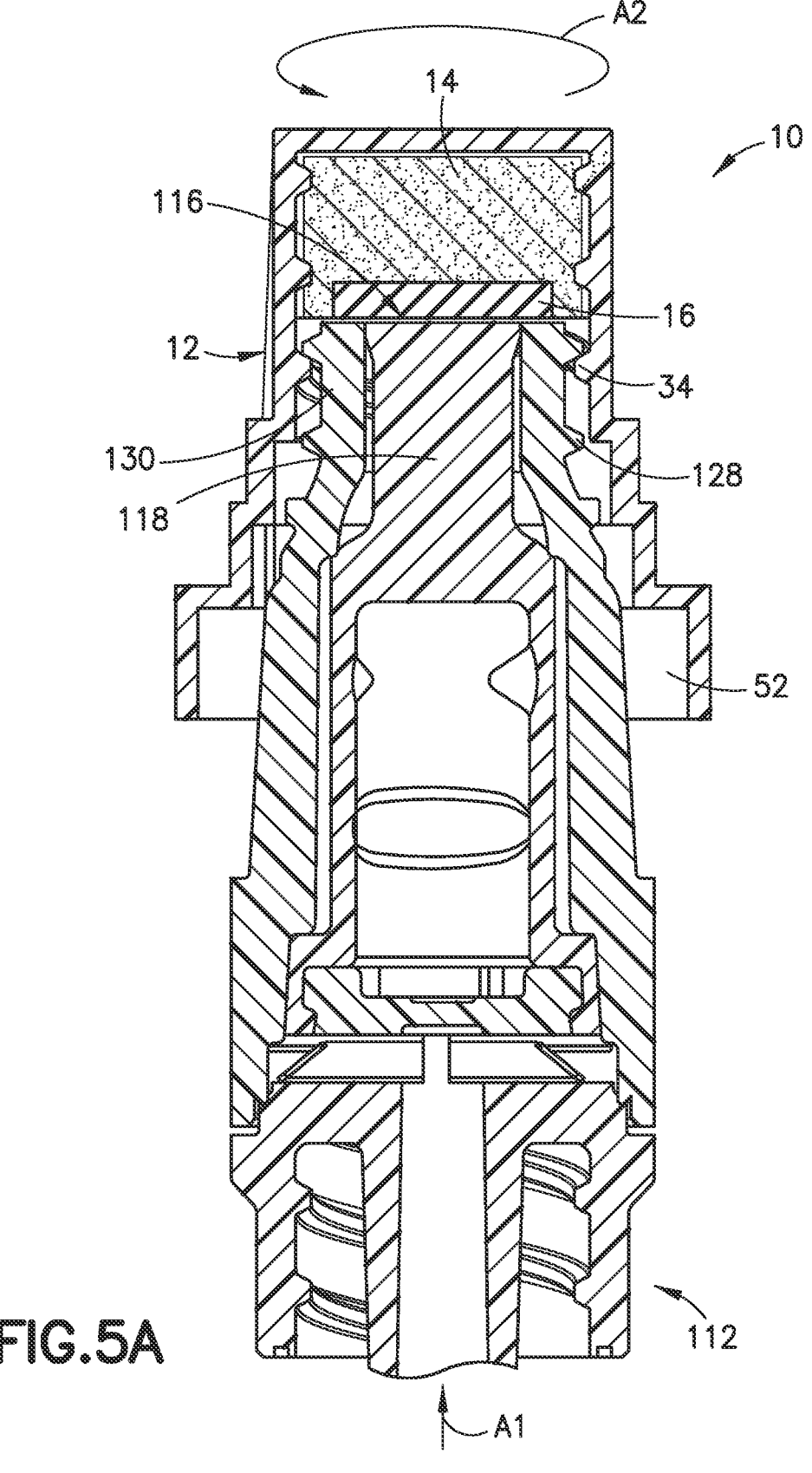
FIG. 5A is a front cross-sectional view of a female luer connector inserted into the universal cap of FIG. 2A, according to an aspect of the disclosure.

In some examples, the absorbent support 14 can be a porous foam or sponge capable of absorbing the cleaning or disinfecting solution. For example, the foam material can be a Plastazote® foam, which is an engineered polymer foam by Zotefoams PCL. Desirably, a porosity of the absorbent support 14 should be optimized so that the material is abrasive enough to scrub or mechanically remove objects from surfaces of the connectors 110, 112, while, at the same time, limiting ingress of cleaning or disinfecting solution into portions of the connectors 110, 112. Further, a height of the absorbent support 14 and/or amount of cleaning or disinfecting solution contained therein can be optimized for use with connectors 110, 112 of different lengths (e.g., for both tall and short connectors). As used herein, a "short connector" refers to a connector that does not insert very far into the cap 10. A "tall connector" refers to a connector that inserts into the cap 10 by a substantial distance, such that a distal end of the connector is proximate to the top wall 24 of the housing 12. For example, short connectors 110, 112 are shown in FIGS. 4A-4C and 5B. Tall connectors 110, 112 are shown in FIGS. 4D and 5A. In general, the height of the absorbent support 14 and amount of cleaning solution contained therein should be large enough so that sufficient cleaning solution is released from the absorbent support 14 when the cap 10 is attached to a short connector 110, 112 to disinfect surfaces of the short connector 110, 112. However, the height of the absorbent support 14 and amount of cleaning solution may be somewhat limited so that liquid ingress into a lumen of the connector 110, 112 does not occur when the cap 10 is attached to a taller connector 110, 112.

The absorbent support 14 can be provided (i.e., pre-soaked) with the cleaning or disinfecting solution. For example, the cleaning or disinfecting solution can be an antimicrobial, anti-fungal, antibacterial, or antiviral solution that cleans and sterilizes surfaces of the connectors 110, 112. In some examples, the cleaning solution can be isopropyl alcohol (IPA), such as about 70% isopropyl alcohol (IPA). In other examples, the cleaning solution can be about 0.5% to about 3.5% chlorhexidine gluconate alone or in combination with about 70% IPA. A chlorohexidine composition may be beneficial because it has a slower evaporation rate than IPA and, therefore, provides a more persistent disinfectant activity after the cap 10 is removed from the connector 110, 112 and before the VAD is connected to the hub, port, or valve.

In some examples, the absorbent support 14 comprises a cavity 40 extending axially inwardly from an end surface of the absorbent support 14. For example, the cavity 40 can be a cylindrical cavity. The cavity 40 can be sized to receive the seal 16 so that the seal 16 is correctly positioned to contact and seal an end of the connector 110, 112, when the connector 110, 112 is inserted into the housing 12. The seal 16 can be formed from a material that prevents fluid, such as the cleaning solution, from entering the connector 110, 112. For example, the seal 16 can comprise a non-porous closed cell foam that is denser and/or more rigid than the foam used for the absorbent support 14.

As shown in FIG. 2D, the cap 10 can also include a removable protective cover 42 attached to the open bottom end 20 of the housing 12 for protecting an interior of the housing 12 and the absorbent support 14 contained therein prior to use. The protective cover 42 can comprise a sheet, such as a polymer film, with adhesive on a first side of the sheet for removably mounting the protective cover 42 to the open bottom end 20 of the housing 12. Alternatively, the protective cover 42 can be removably mounted to the bottom end 20 of the cap 10 by heat sealing. The protective cover 42 can be slightly larger than the bottom end 20 of the housing 12, so that the cover 42 can be easily grasped by the practitioner to remove the protective cover 42 from the cap 10 prior to use. The protective cover 42 can be formed from a material that is impervious or substantially impervious to air, so that the cleaning solution on the absorbent support 14 does not evaporate or dry-out prior to use of the cap 10. Accordingly, the protective cover 42 increases a shelf life of the cap 10, as well as prevents microbes and other debris from collecting in the cap 10 prior to use.

The cap 10 can be provided in a number of different packages or containers, as are known in the art. For example, caps 10 can be packaged individually in paper or plastic packages. In other examples, multiple caps 10 can be provided together in a single packaging. For example, multiple caps 10 can be provided on strips of paper or plastic film configured to be hung from, for example, an IV pole. Multiple caps 10 can also be packaged in blisters or flow wrap on a strip or card to protect the caps if dropped prior to use.

Methods of Use for Universal Caps

Figure 5B:
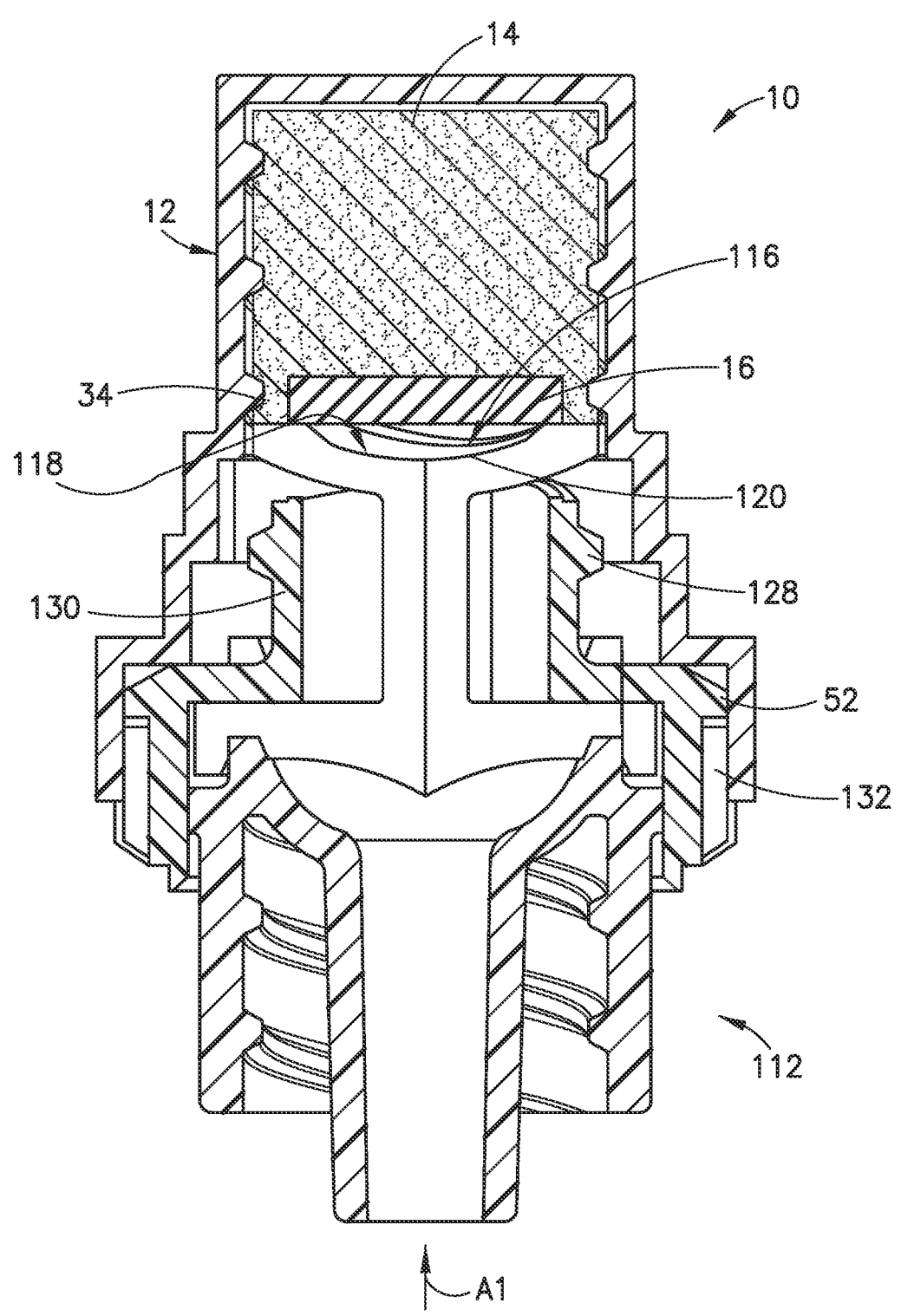
FIG. 5B is a front cross-sectional view of another exemplary female luer connector inserted into the universal cap of FIG. 2A, according to an aspect of the present disclosure.

As previously described, the cap 10 of the present disclosure is configured to be connected to a variety of different types of male connectors 110 and female connectors 112. FIGS. 4A-4D show the cap 10 attached to different examples of male connectors 110. FIGS. 5A and 5B show the cap 10 connected to different examples of female connectors 112. Specifically, in FIGS. 4A-4C, the cap 10 is connected to a short male connector 110, such as the BD Q-Syte™ connector, by Becton Dickinson and Company. FIG. 4D shows the cap 10 attached to a taller male connector 110, such as the BD MaxPlus™ connector by Becton Dickinson and Company. FIG. 5A shows the cap 10 attached to a tall female connector 112 (e.g., the BD MaxPlus™ connector). FIG. 5B shows the cap 10 attached to a short female connector 112 (e.g., BD Q-Syte™) Exemplary male connectors 110 and female connectors 112 including features of the BD Q-Syte™ connectors are described in U.S. Pat. No. 7,806, 890, entitled "Vascular Access Device Volume Displacement", which is incorporated by reference herein in its entirety.

In order to connect the cap 10 to a male connector 110, the practitioner first removes any packaging and the protective cover 42 from the cap 10. The practitioner then pushes the cap 10 onto the male connector 110 in a direction of arrow A1 (shown in FIGS. 4A-4D). The stem 114 of the male connector 110 contacts and is sealed by the seal 16 enclosed within the housing 12 of the cap 10. Contact between the male connector 110 and the seal 16 or absorbent support 14 creates an interference engagement that secures the cap 10 to the male connector 110. Also, contact between an outer surface of the male connector 110 and the interfering protrusions 50, such as the crushable ribs, extending inwardly from the inner surface 52 of the sidewall 22 of the housing 12 forms an additional interference or friction engagement between the male connector 110 and the cap 10 for securing the cap 10 to the male connector 110. As previously described, the contact between the male connector 110 and the absorbent support 14 can also release cleaning solution, causing the cleaning solution to contact and sterilize surfaces of the male connector 110. In particular, the cleaning solution can contact both an outer surface of the stem 114 of the male connector 110 and the inner surface 126 of the annular shield 122 of the male connector 110, thereby disinfecting and sterilizing both surfaces 114, 126. Finally, direct contact between surfaces of the male connector 110 and abrasive portions of the absorbent support 14 or seal 16 can mechanically remove microbes, debris, and other contaminants from surfaces of the male connector 110, contributing to the disinfecting effects provided by the cap 10. In order to remove the cap 10 from the male connector 110, the practitioner grasps the cap 10 and pulls it away from the male connector 110 with sufficient force to overcome the interference and/or friction engagement between the male connector 110 and portions of the cap 10. Once the cap 10 is removed, a VAD can be connected to the hub, port, or valve through the male connector 110, as previously described.

FIG. 5A shows the cap 10 mounted to or inserted over a tall female connector 112. In order to connect the cap 10 to a tall female connector 112, the practitioner first removes any packaging from the cap 10 and removes the protective cover 42 from the bottom end 20 of the housing 12. The female connector 112 is inserted into the cap 10 (as shown by arrow A1 in FIG. 5A), to bring the threads 128 of the female connector 112 into contact with the threads 34 on the inner surface 32 of the sidewall 22 of the housing 12. As previously described, the flexible portion 26 of the sidewall 22 may deform to accommodate the size and shape of the female connector 112. Once the threads 128 of the female connector 112 are in contact with the threads 34 of the housing 12, the practitioner rotates the cap 10 about the female connector 112, as shown by arrow A2 in FIG. 5A, in order to secure the cap 10 to the connector 112. Rotation of the cap 10 can cause the absorbent support 14 to compress and/or to release the cleaning solution, which contacts surfaces of the female connector 112 to sterilize the surfaces of the connector 112. In particular, the cleaning solution may contact and sterilize portions of the septum 118 and outer surface 130 of the female connector 112. In order to remove the cap 10, the practitioner rotates the cap 10 in an opposite direction, causing threads 34 of the housing sidewall 22 to release from the threads 128 of the female connector 112. Once the threads 34, 128 are released, the practitioner can pull the cap 10 away from the female connector 112.

FIG. 5B shows the cap 10 mounted to or inserted in a short female connector 112, such as a female BD Q-Syte™. In order to connect the cap 10 to the short female connector 112, the practitioner pushes the cap 10 onto the short female connector 112 in a direction of arrow A1 (shown in FIG. 5B). The opening 116 and/or septum 118 of the female connector 112 contacts and is sealed by the seal 16 enclosed within the housing 12 of the cap 10. Contact between the female connector 112 and the seal 16 or absorbent support 14 creates an interference engagement that secures the cap 10 to the female connector 112. However, the threads 128 of the female connector 112 do not engage the thread 34 in the rigid portion 30 of the housing 12. Instead, the vertical ridges 132 near the base of the female connector 112 can contact the inner surface 52 of the sidewall 22 to form an additional interference or friction engagement between the female connector 112 and the cap 10 for securing the cap 10 to the female connector 112. As previously described, the contact between the female connector 112 and the absorbent support 14 can also release cleaning solution, causing the cleaning solution to contact and sterilize surfaces of the female connector 112. In order to remove the cap 10 from the short female connector 112, the practitioner grasps the cap 10 and pulls it away from the female connector 112 with sufficient force to overcome the interference and/or friction engagement between the female connector 112 and portions of the cap 10.

Methods of Manufacture for Universal Caps

The universal cap 10 of the present disclosure is desirably a single-use product that can be manufactured inexpensively and efficiently by a simple molding process requiring only a few assembly steps. An exemplary simple manufacturing method for the universal caps 10 is shown in the flow chart of FIG. 6.

Figure 6:
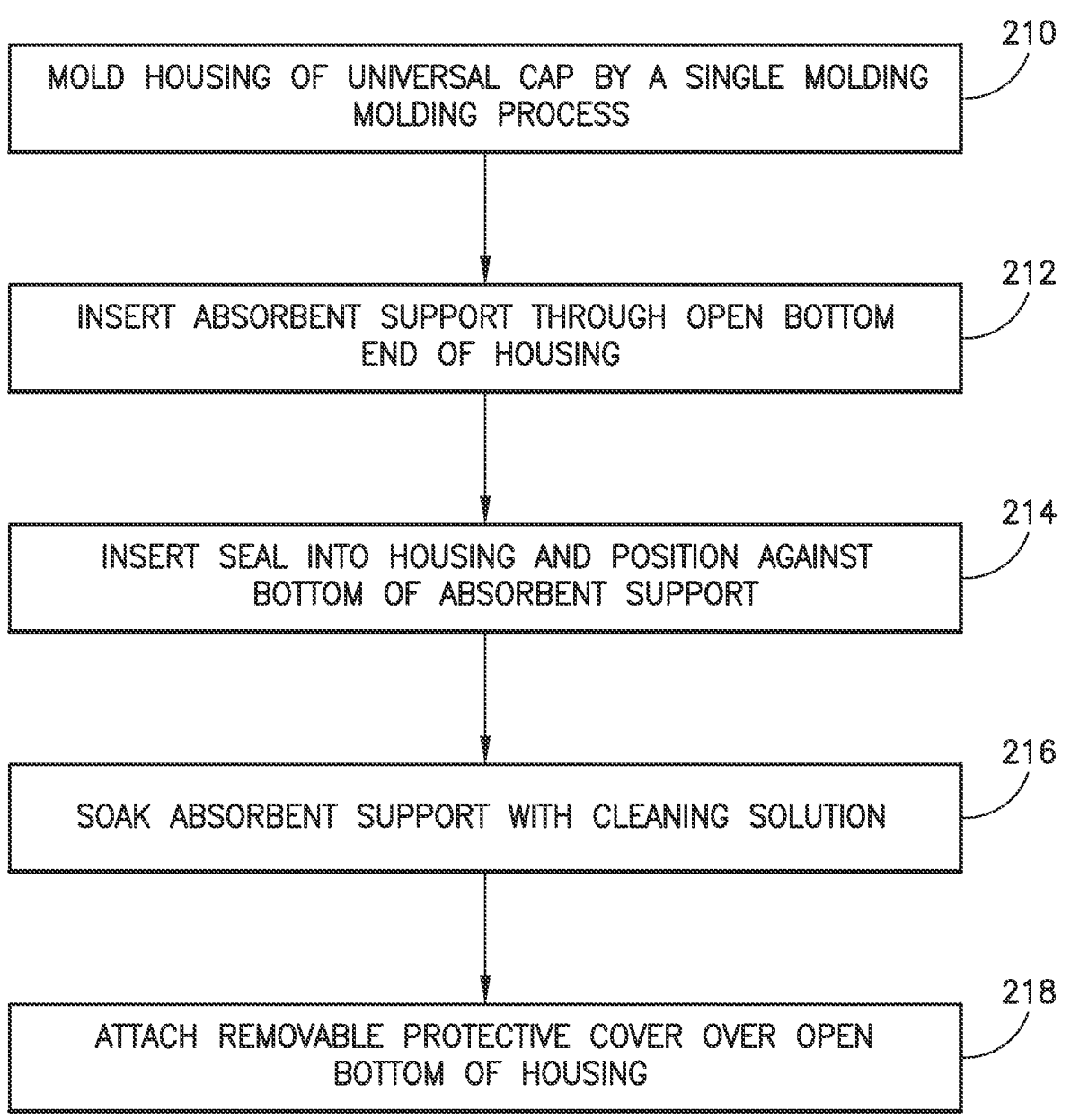
FIG. 6 is a flow chart showing a method of manufacture for a universal cap, according to an aspect of the present disclosure.

As shown in FIG. 6, the method for making a universal cap 10 configured to engage at least a first connector (e.g., a female luer connector 112) and a second connector (e.g., a male luer connector 110) of different types comprises, at step 210, molding a housing 12 of the universal cap 10, as a single molding process that produces an integrally formed housing 12. The housing 12 can be the previously described housing 12 shown, for example, in FIGS. 2A-3C. For example, the housing 12 can comprise the first or top end 18, which can be covered by a first end or top wall 24, the open second or bottom end 20, and the sidewall 22 extending between the top end 18 and the bottom end 20. The housing 12 can further comprise the interfering protrusions 50 extending inwardly from the inner surface 52 of the sidewall 22. As previously described, the interfering protrusions 50 can be configured to provide an interference engagement with the male connector 110. In some examples, the interfering protrusions 50 can be crushable ribs extending over the inner surface 52 of the sidewall 22. The crushable ribs can be configured to be crushed by an outer surface of the male connector 110, thereby forming the interference engagement between the male connector 110 and the cap 10.

In some examples, the housing 12 of the cap 10 is molded by injection molding, wherein a polymer precursor material is injected into a single mold in a single molding process. Desirably, the single molding process forms all parts of the housing 12, including the interfering protrusions 50, such that no additional processing or machining of the housing 12 is needed. More specifically, in some examples, molding the housing 12 comprises depositing a flowable polymer precursor into a mold of an injection molding machine. The method further comprises curing the polymer precursor to form a rigid thermoplastic polymer, such as polyester, polycarbonate, polypropylene, polyethylene, polyethylene terephthalate, or acrylonitrile butadiene styrene.

At step 212, the method further comprises, after molding of the housing 12 is complete, inserting the absorbent support 14 through the open bottom end 20 of the housing 12, such that the absorbent support 14 is seated against the top end wall 24 of the housing 12. As previously described, the absorbent support 14 can be a cylindrical member sized to be received within a substantially cylindrical cavity defined by a portion of the inner surface 52 of the sidewall 22 and a bottom surface of the top end wall 24 of the housing 12.

At step 214, the method further comprises inserting the seal 16 against a bottom end of the absorbent support 14. The seal 16 can be a disk-shaped member comprising a closed cell foam. As previously described, when the male connector 110 or the female connector 112 is inserted into the cap 10, the seal 16 is configured to cover an opening of the connector 110, 112, preventing cleaning solution or other fluids from flowing through the opening and into a lumen of the connector 110, 112.

At step 216, the method further comprises soaking the absorbent support 14 with a cleaning or disinfecting solution, such as an antimicrobial, anti-fungal, antibacterial, or antiviral composition. In some examples, the cleaning or disinfecting solution can comprise about 0.5% to about 3.5% chlorhexidine gluconate, about 60% to 85% isopropyl alcohol (IPA), or combinations thereof. The absorbent support 14 can be soaked with the cleaning or disinfecting solution before inserting the absorbent support 14 into the cap 10. In other examples, the cleaning or disinfecting solution can be added after the absorbent support 14 and/or seal 16 are in place in the cap 10. For example, the cleaning or disinfecting solution can be poured into the cap 10 through the open bottom end 20 so that it can be absorbed by the absorbent support 14.

At step 218, the method can further comprise, after the cleaning or disinfecting solution is absorbed by the absorbent support 14, attaching a removable protective cover 42 over the open bottom end 20 of the housing 12, thereby forming a sealed universal cap 10. In some examples, the protective cover 42 comprises a film with adhesive on a top side of the film for removably mounting or attaching the film to the open bottom end 20 of the housing 12. Alternatively, the protective cover 42 or film can be attached to the open bottom end 20 of the housing 12 by heat sealing. Once the protective cover 42 is in place, the cap 10 is essentially ready for use. Accordingly, the completed caps 10 can be packaged either individually into paper or plastic packages or multiple caps 10 can be packaged together into a single packaging. For example, multiple caps 10 can be provided on strips of paper or plastic film configured to be hung from, for example, an IV pole. Multiple caps 10 can also be packaged in blisters or flow wrap on a strip or card to protect the caps 10 if dropped prior to use.

While examples of the universal cap and methods of use of the present disclosure are shown in the accompanying figures and described hereinabove in detail, other examples will be apparent to, and readily made by, those skilled in the art without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. A cap configured to engage at least a first connector and a second connector of different types, the cap comprising:
   a housing comprising a first end, an open second end, a sidewall extending between the first end and the second end, and a plurality of interfering protrusions extending inwardly from an inner surface of the sidewall configured to provide an interference engagement with the first connector or the second connector;
   an absorbent support positioned in the housing configured to contact portions of the first connector or the second connector, when the first connector or the second connecter is inserted into the housing; and
   a seal mounted to a portion of the absorbent support configured to cover an opening of the first connector or the second connector when the first connector or the second connector is inserted into the housing.

2. The cap of claim 1, wherein the cap is configured to be secured to the second connector by the interference engagement between the interfering protrusions and the second connector.

3. The cap of claim 2, wherein, when the first connector is inserted into the housing, the plurality of interfering protrusions do not engage the first connector.

4. The cap of claim 2, wherein the housing further comprises threads on the inner surface of the sidewall, and wherein the first connector is connected to the cap by an engagement between the threads of the housing and corresponding protrusions or grooves on the first connector.

5. The cap of claim 1, wherein the plurality of interfering protrusions comprises a plurality of crushable ribs extending over the inner surface of the sidewall of the housing, the ribs being configured to be crushed by an outer surface of the second connector, thereby forming the interference engagement between the second connector and the cap.

6. The cap of claim 5, wherein the plurality of crushable ribs extends substantially parallel to a longitudinal axis of the housing.

7. The cap of claim 5, wherein the plurality of crushable ribs is equidistantly spaced about a circumference of the inner surface of the housing.

8. The cap of claim 5, wherein the plurality of crushable ribs comprises a rounded surface curving about a longitudinal axis of the rib.

9. The cap of claim 1, wherein the plurality of interfering protrusions comprises (i) a first group of the plurality of interfering protrusions in a first tier of the housing having a first inner diameter, and (ii) a second group of the plurality of interfering protrusions in a second tier of the housing having a second inner diameter different from the first inner diameter.

10. The cap of claim 9, wherein the first group of the plurality of interfering protrusions is spaced about the first tier of the housing and the second group of the plurality of interfering protrusions is spaced about the second tier of the housing.

11. The cap of claim 10, wherein the plurality of protrusions comprises crushable ribs extending substantially parallel to a longitudinal axis of the housing, and wherein the first group of the plurality of interfering protrusions is not axially aligned with the second group of the plurality of interfering protrusions.

12. The cap of claim 1, wherein the sidewall of the housing comprises a flexible portion proximate to the second end of the housing configured to press against and deform to accommodate portions of the first connector or the second connector when the first connector or the second connector is inserted into the housing, wherein the flexible portion of the sidewall has a variable inner diameter that is widest at the second end of the housing and becomes narrower towards the first end of the housing, and wherein the flexible portion comprises a plurality of tiers having different inner diameters.

13. The cap of claim 1, wherein the housing is a single-molded part comprising a rigid thermoplastic polymer comprising polyester, polycarbonate, polypropylene, polyethylene, polyethylene terephthalate, or acrylonitrile butadiene styrene.

14. The cap of claim 1, wherein the absorbent support comprises a cylindrical member sized to be received within a substantially cylindrical cavity defined by a portion of the inner surface of the sidewall of the housing.

15. The cap of claim 1, further comprising a cleaning or disinfecting solution absorbed by the absorbent support, wherein the cleaning or disinfecting solution comprises about 0.5% to about 3.5% chlorhexidine gluconate, about 60% to 85% isopropyl alcohol (IPA), or combinations thereof, and wherein the seal is configured to prevent or restrict the cleaning or disinfecting solution from flowing from the absorbent support into a lumen of the first connector or the second connector engaged to the cap.

16. The cap of claim 1, further comprising a removable protective cover attached to the open second end of the housing for protecting an interior of the housing and the absorbent support prior to use.

17. The cap of claim 1, wherein the housing comprises:

a first tier having a first inner diameter, a second tier having a second inner diameter larger than the first inner diameter adjacent to the first flexible tier, and a third tier between the second tier and the open second end of the housing having a third inner diameter, which is larger than the first inner diameter or the second inner diameter.

18. The cap of claim 17, wherein the plurality of interfering protrusions is positioned on the first tier and/or the second tier of the housing, and wherein the third tier does not include interfering protrusions.

19. The cap of claim 18, wherein the housing further comprises a threaded rigid portion between the first tier and the first end of the housing, the threaded rigid portion comprising threads extending inwardly from the inner surface of the sidewall of the housing configured to engage corresponding threads of the first connector.

20. A method for making a universal cap configured to engage at least a first connector and a second connector of different types, the method comprising:

molding a housing of the universal cap, as a single molding process that produces an integrally formed housing, wherein the housing comprises a first end covered by a first end wall, an open second end, a sidewall extending between the first end and the second end, and a plurality of interfering protrusions extending inwardly from an inner surface of the sidewall configured to provide an interference engagement with the first connector or the second connector;

inserting an absorbent support through the open second end of the housing such that the absorbent support is seated against the first end wall of the housing; and inserting a seal against an end of the absorbent support.

21. The cap of claim 1, wherein the seal comprises a non-porous closed cell foam.

* * * * *